(12) United States Patent
Zukowski et al.

(10) Patent No.: US 12,194,119 B2
(45) Date of Patent: *Jan. 14, 2025

(54) DUAL PHASE PRODUCTS

(71) Applicant: The Procter & Gamble Company, Cincinnati, OH (US)

(72) Inventors: Joseph Michael Zukowski, Singapore (SG); Sudeep Chakravarty, Singapore (SG); Yu Wang, Singapore (SG); Suxuan Gong, Singapore (SG)

(73) Assignee: The Procter & Gamble Company, Cincinnati, OH (US)

(*) Notice: Subject to any disclaimer, the term of this patent is extended or adjusted under 35 U.S.C. 154(b) by 586 days.

This patent is subject to a terminal disclaimer.

(21) Appl. No.: 17/126,321

(22) Filed: Dec. 18, 2020

(65) Prior Publication Data

US 2021/0128422 A1 May 6, 2021

Related U.S. Application Data

(63) Continuation of application No. PCT/US2019/039676, filed on Jun. 28, 2019.
(Continued)

(51) Int. Cl.
*A61K 8/11* (2006.01)
*A45D 40/24* (2006.01)
(Continued)

(52) U.S. Cl.
CPC ............... *A61K 8/11* (2013.01); *A45D 40/24* (2013.01); *A61K 8/042* (2013.01); *A61K 8/19* (2013.01); *A61K 8/20* (2013.01); *A61K 8/362* (2013.01); *A61K 8/365* (2013.01); *A61K 8/368* (2013.01); *A61K 8/44* (2013.01); *A61K 8/4973* (2013.01); *A61K 8/55* (2013.01); *A61K 8/675* (2013.01); *A61K 8/731* (2013.01); *A61K 8/8152* (2013.01);
(Continued)

(58) Field of Classification Search
None
See application file for complete search history.

(56) References Cited

U.S. PATENT DOCUMENTS 4,617,148 A * 10/1986 Shields ................ C11D 17/003
510/159
4,773,562 A 9/1988 Gueret
(Continued)

FOREIGN PATENT DOCUMENTS

CA 2215179 C 2/2007
CA 2215051 C 11/2008
(Continued)

OTHER PUBLICATIONS

Dr Siew' "Product Review: L'Oreal Revitalift Laser X3 Anti-Aging Double Serum", an internet article published on Sep. 30, 2017 and obtained from the website: https://drsiew.com/loreal-revitalift-laser-x3-anti-aging-double-serum-review/ (2017).*
(Continued)

*Primary Examiner* — Sin J Lee
(74) *Attorney, Agent, or Firm* — Alexandra S. Anoff

(57) ABSTRACT

A discrete dispensed product comprising a first portion; and a second portion at least partially surrounding the first portion provides a premium and distinct appearance to consumers.

16 Claims, 26 Drawing Sheets

Related U.S. Application Data

(60) Provisional application No. 62/691,656, filed on Jun. 29, 2018.

(51) Int. Cl.

| | | |
|---|---|---|
| *A61K 8/04* | (2006.01) | |
| *A61K 8/19* | (2006.01) | |
| *A61K 8/20* | (2006.01) | |
| *A61K 8/362* | (2006.01) | |
| *A61K 8/365* | (2006.01) | |
| *A61K 8/368* | (2006.01) | |
| *A61K 8/44* | (2006.01) | |
| *A61K 8/49* | (2006.01) | |
| *A61K 8/55* | (2006.01) | |
| *A61K 8/67* | (2006.01) | |
| *A61K 8/73* | (2006.01) | |
| *A61K 8/81* | (2006.01) | |
| *A61Q 19/00* | (2006.01) | |
| *B05B 7/06* | (2006.01) | |
| *B05C 17/005* | (2006.01) | |

(52) U.S. Cl.
CPC ............ *A61K 8/8158* (2013.01); *A61Q 19/00* (2013.01); *B05B 7/06* (2013.01); *B05C 17/00516* (2013.01); *B05C 17/00553* (2013.01); *A45D 2200/058* (2013.01); *A61K 2800/10* (2013.01); *A61K 2800/20* (2013.01); *A61K 2800/262* (2013.01); *A61K 2800/42* (2013.01); *A61K 2800/48* (2013.01); *A61K 2800/592* (2013.01); *A61K 2800/5922* (2013.01); *A61K 2800/87* (2013.01)

(56) References Cited

U.S. PATENT DOCUMENTS

| | | | |
|---|---|---|---|
| 4,993,595 A | 2/1991 | Bertram et al. | |
| 5,020,694 A | 6/1991 | Pettengill | |
| 5,137,178 A | 8/1992 | Stokes et al. | |
| 5,252,312 A | 10/1993 | Gentile et al. | |
| 5,289,949 A | 3/1994 | Gentile | |
| 5,332,124 A | 7/1994 | Cancro et al. | |
| 5,398,846 A | 3/1995 | Corba et al. | |
| 5,611,463 A | 3/1997 | Favre | |
| 5,645,193 A | 7/1997 | Gentile et al. | |
| 5,740,947 A | 4/1998 | Flaig et al. | |
| 5,794,819 A | 8/1998 | Smith | |
| 5,862,949 A | 1/1999 | Markey et al. | |
| 5,899,360 A | 5/1999 | Mack et al. | |
| 5,954,213 A | 9/1999 | Gerhart et al. | |
| 6,039,215 A | 3/2000 | Bell | |
| 6,063,223 A | 5/2000 | Klauke et al. | |
| 6,082,588 A | 7/2000 | Markey et al. | |
| 6,135,323 A | 10/2000 | Chen et al. | |
| 6,161,729 A | 12/2000 | Gentile et al. | |
| 6,223,943 B1 | 5/2001 | Richmond et al. | |
| 6,230,935 B1 | 5/2001 | Mack et al. | |
| 6,308,862 B1 | 10/2001 | Fillmore et al. | |
| 6,308,863 B1 | 10/2001 | Harman | |
| 6,454,135 B1 | 9/2002 | Brozell | |
| 6,499,900 B1 | 12/2002 | Brozell | |
| 6,583,103 B1 | 6/2003 | Klinkhammer | |
| 6,585,984 B1 | 7/2003 | Scott et al. | |
| 6,695,510 B1 | 2/2004 | Look et al. | |
| 6,722,532 B2 | 4/2004 | Lasserre et al. | |
| 6,758,411 B2 | 7/2004 | Conway et al. | |
| 6,858,984 B2 | 2/2005 | Yamashita | |
| 7,622,132 B2 * | 11/2009 | Lee ....................... | A61K 8/894 424/455 |
| 7,654,415 B2 | 2/2010 | Van Der Heijden | |
| 7,665,631 B2 | 2/2010 | Pikowski | |
| 8,021,064 B2 | 9/2011 | Gueret | |
| 8,413,849 B2 | 4/2013 | Flores | |
| 9,271,912 B2 | 3/2016 | Fernandez Prieto et al. | |
| 9,303,820 B2 | 4/2016 | Miller | |
| 9,551,332 B2 | 1/2017 | Burrowes et al. | |
| 9,586,714 B2 | 3/2017 | Kountotsis | |
| 9,693,619 B2 | 7/2017 | Ki | |
| 9,776,787 B2 | 10/2017 | Nakajima | |
| 10,029,267 B2 | 7/2018 | Connolly et al. | |
| 10,799,431 B2 | 10/2020 | Boswell et al. | |
| 10,959,933 B1 | 3/2021 | Zhang et al. | |
| 10,973,702 B2 | 4/2021 | Smith et al. | |
| 11,571,375 B2 | 2/2023 | Zukowski et al. | |
| 11,583,479 B2 | 2/2023 | Zukowski et al. | |
| 11,583,488 B2 | 2/2023 | Zhang et al. | |
| 2002/0041788 A1 | 4/2002 | Look et al. | |
| 2002/0074347 A1 | 6/2002 | Murray et al. | |
| 2002/0197228 A1 | 12/2002 | Lasala et al. | |
| 2003/0089738 A1 | 5/2003 | Peterson | |
| 2003/0121936 A1 | 7/2003 | De Laforcade | |
| 2004/0175347 A1 | 9/2004 | Bissett | |
| 2004/0251274 A1 | 12/2004 | Ponton | |
| 2005/0192187 A1 | 9/2005 | Wagner et al. | |
| 2005/0215155 A1 | 9/2005 | Young et al. | |
| 2005/0279755 A1* | 12/2005 | Jansen ................. | G07F 11/44 221/9 |
| 2006/0021996 A1 | 2/2006 | Scott et al. | |
| 2006/0049278 A1 | 3/2006 | Hoshino | |
| 2006/0065674 A1 | 3/2006 | Lasserre et al. | |
| 2006/0198686 A1 | 9/2006 | Hetzel | |
| 2007/0014823 A1 | 1/2007 | Iwata | |
| 2007/0029344 A1 | 2/2007 | Schymitzek et al. | |
| 2007/0045343 A1 | 3/2007 | Lasserre et al. | |
| 2007/0158461 A1 | 7/2007 | Rymer et al. | |
| 2009/0028809 A1 | 1/2009 | Cetti et al. | |
| 2009/0152294 A1 | 6/2009 | Mizell | |
| 2009/0324520 A1 | 12/2009 | Cetti et al. | |
| 2010/0025427 A1 | 2/2010 | Chiou et al. | |
| 2010/0034574 A1 | 2/2010 | Zhang | |
| 2010/0119562 A1* | 5/2010 | Hilliard, Jr. ............. | A61Q 5/02 424/401 |
| 2010/0155424 A1 | 6/2010 | Tsai | |
| 2012/0014849 A1 | 1/2012 | Killen et al. | |
| 2012/0316532 A1 | 12/2012 | Mccormick | |
| 2013/0280356 A1 | 10/2013 | Stella et al. | |
| 2014/0044934 A1 | 2/2014 | Bills et al. | |
| 2016/0128915 A1 | 5/2016 | Konno et al. | |
| 2016/0318055 A1 | 11/2016 | Scott et al. | |
| 2016/0374919 A1 | 12/2016 | Hakozaki et al. | |
| 2016/0374933 A1 | 12/2016 | Tanner et al. | |
| 2017/0028422 A1 | 2/2017 | Martines | |
| 2017/0367461 A1 | 12/2017 | Tsubouchi et al. | |
| 2018/0022526 A1 | 1/2018 | Demarest et al. | |
| 2018/0044099 A1 | 2/2018 | Nakajima et al. | |
| 2018/0243770 A1 | 8/2018 | Pointel et al. | |
| 2018/0319573 A1 | 11/2018 | Yamaguchi et al. | |
| 2019/0038523 A1 | 2/2019 | Konno et al. | |
| 2019/0039806 A1 | 2/2019 | De Cleir | |
| 2020/0000689 A1 | 1/2020 | Zukowski et al. | |
| 2021/0128436 A1 | 5/2021 | Zukowski et al. | |
| 2021/0137244 A1 | 5/2021 | Zukowski et al. | |
| 2023/0165767 A1 | 6/2023 | Ehrman et al. | |

FOREIGN PATENT DOCUMENTS

| | | |
|---|---|---|
| CN | 1213634 A | 4/1999 |
| CN | 1427708 A | 7/2003 |
| CN | 101784252 A | 7/2010 |
| CN | 107921448 A | 4/2018 |
| CN | 108289797 A | 7/2018 |
| DE | 20318444 U1 | 3/2004 |
| EP | 0873945 B1 | 8/2003 |
| FR | 2647093 B1 | 9/1994 |
| JP | S60113162 A | 6/1985 |
| JP | H02102388 A | 4/1990 |
| JP | H05228218 A | 9/1993 |
| JP | H0642449 A | 2/1994 |
| JP | H09327501 A | 12/1997 |
| JP | 2000007558 A | 1/2000 |
| JP | 2001520086 A | 10/2001 |
| JP | 2002047135 A | 2/2002 |

(56) References Cited

FOREIGN PATENT DOCUMENTS

| | | |
|---|---|---|
| JP | 2002068925 A | 3/2002 |
| JP | 2002539150 A | 11/2002 |
| JP | 2003190764 A | 7/2003 |
| JP | 20030071480 A | 9/2003 |
| JP | 2003306412 A | 10/2003 |
| JP | 2004002207 A | 1/2004 |
| JP | 2005035631 A | 2/2005 |
| JP | 2005089337 A | 4/2005 |
| JP | 2005239600 A | 9/2005 |
| JP | 2011006374 A | 1/2011 |
| JP | 2011032181 A | 2/2011 |
| JP | 2011068600 A | 4/2011 |
| JP | 4944493 B2 | 3/2012 |
| JP | 2012051582 A | 3/2012 |
| JP | 2012148990 A | 8/2012 |
| JP | 2016507592 A | 3/2016 |
| JP | 2016124801 A | 7/2016 |
| JP | 2017095452 A | 6/2017 |
| JP | 2017119698 A | 7/2017 |
| JP | 2017190291 A | 10/2017 |
| KR | 20150086284 A | 7/2015 |
| KR | 101817077 B1 | 1/2018 |
| WO | 2008012191 A1 | 1/2008 |
| WO | 2008014833 A1 | 2/2008 |
| WO | 2014097149 A1 | 6/2014 |
| WO | 2017004102 A1 | 1/2017 |
| WO | 2017057784 A1 | 4/2017 |
| WO | 2017115827 A1 | 7/2017 |

OTHER PUBLICATIONS

PCT Search Report and Written Opinion for PCT/US2019/039676 dated Jan. 27, 2020.
All Office Actions, U.S. Appl. No. 16/456,023.
All Office Actions, U.S. Appl. No. 17/126,373.
All Office Actions, U.S. Appl. No. 17/126,399.
Ewald, Mikala, "7 Luscious Lipsticks for Summer That You're Gonna Love", Retrieved from: https://makeup.allwomenstalk.com/luscious-lipsticks-for-summer-that-youre-gonna-love/, Jul. 25, 2013, 6 Pages.
Zarket, et al., "Onion-like Multilayered Polymer Capsules Synthesized by a Bioinspired inside-out Technique", In Journal of Nature communications, vol. 8, No. 1, Aug. 4, 2017.

* cited by examiner

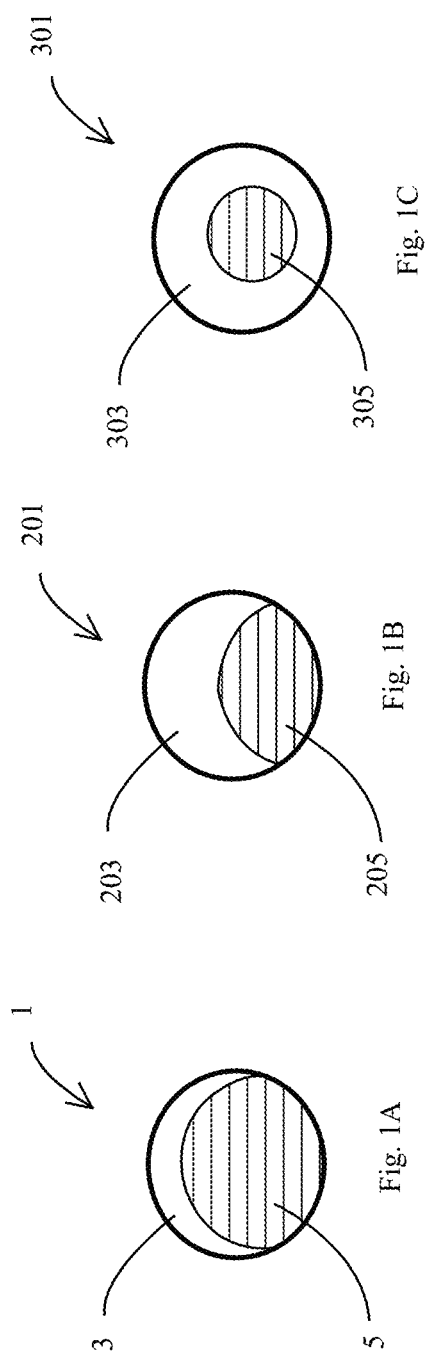
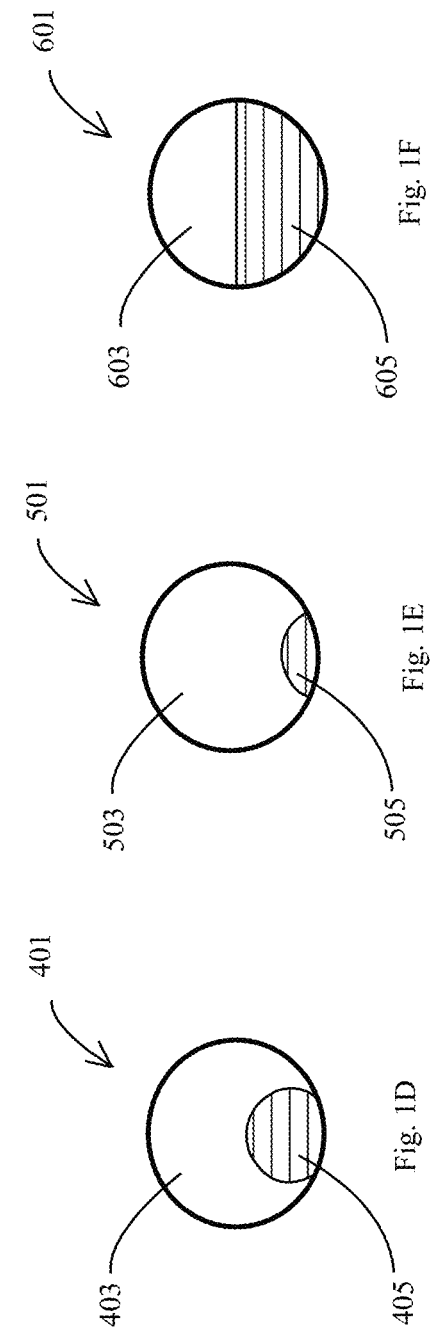

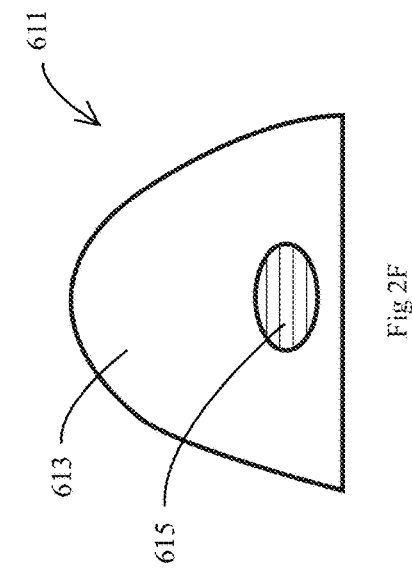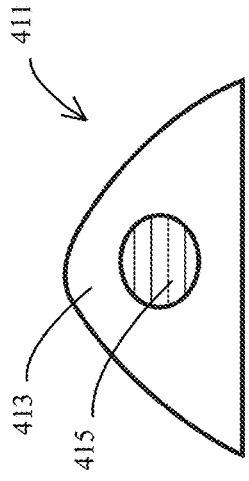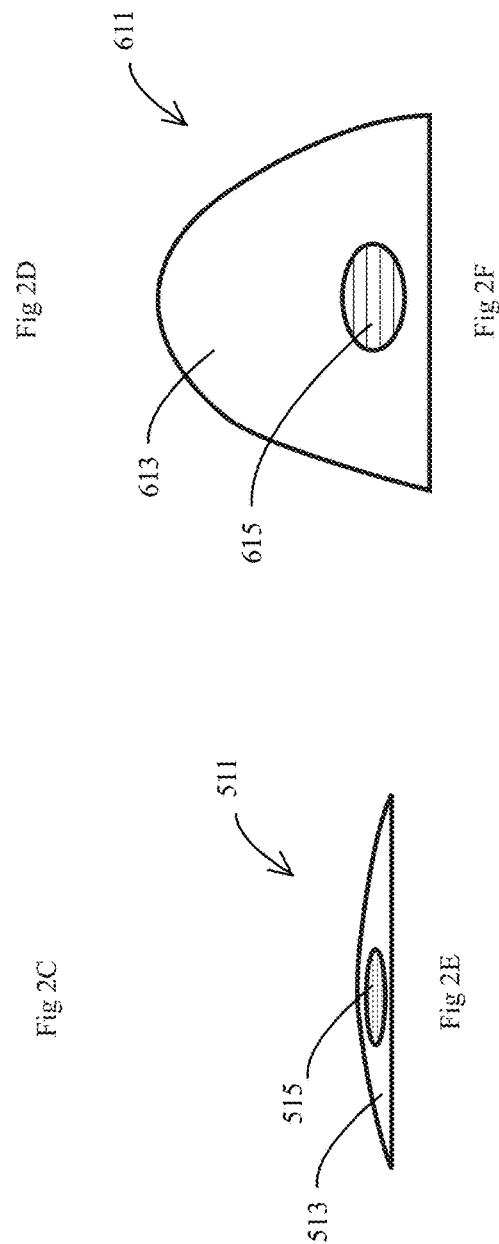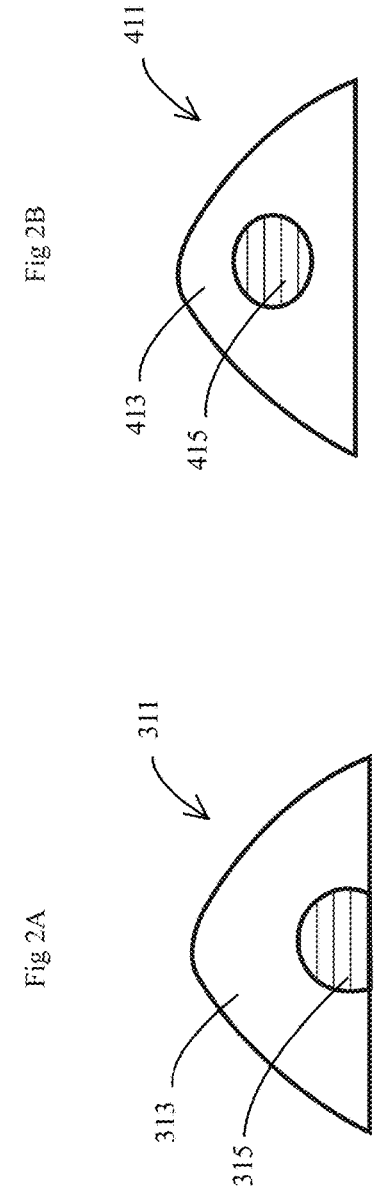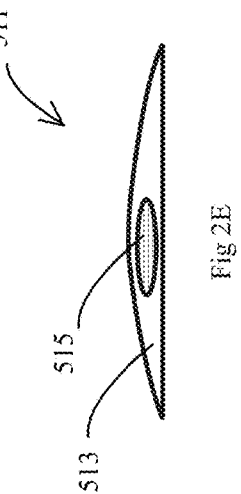

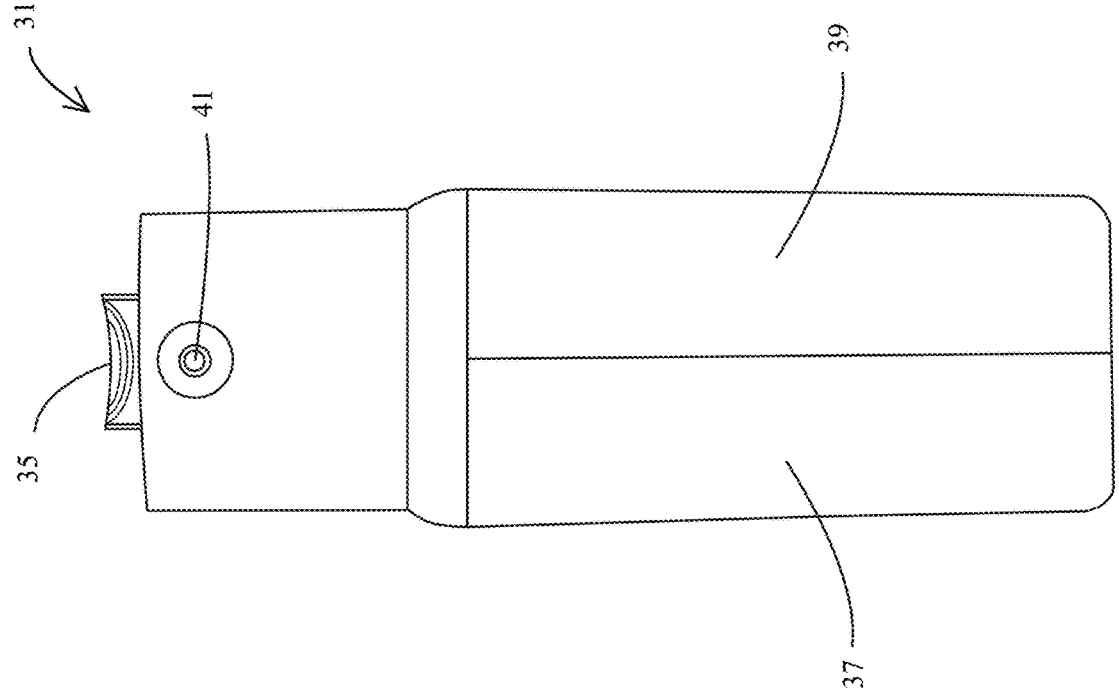

Table 1: Formulation and Data for Comparative Example I

| Trade Name | INCI name | Manufacturer | Comparative Example I | |
|---|---|---|---|---|
| | | | 1st Portion (weight %) | 2nd Portion (weight %) |
| Purified Water | Purified Water | | QS | QS |
| Sepimax Zen | Polyacrylate 6 crosspolymer | Seppic | | |
| Ultrez 20 | Acrylates/C10-30 Alkyl Acrylate Crosspolymer | Lubrizol | 0.363 | 0.400 |
| Aristoflex Silk | Sodium Polyacryloyldimethyl Taurate | Clariant | | |
| AMP Ultra PC 1000 Neutraizing amine | Aminomethyl Propanol | AngusChemie Gmbh | 0.238 | 0.240 |
| Galactomyces Ferment Filtrate | Galactomyces Ferment Filtrate, Butylene Glycol and Methylparaben | P&G | | |
| Disodium EDTA | Disodium EDTA | Nagase ChemTex | 0.100 | 0.100 |

Fig. 7A

| | | Comparative Example I | |
|---|---|---|---|
| Trade Name | INCI name | Manufacturer | 1st Portion (weight %) | 2nd Portion (weight %) |
| Glycerin 99% | Glycerin | P&G Chemicals | 5.000 | 5.000 |
| Xylitol C | Xylitol | Danisco | 3.000 | 3.000 |
| Niacinamide USP | Niacinamide | Western Drugs Limited | 5.000 | 5.000 |
| Probenz SP Powder | Sodium Benzoate | Eastman | 0.050 | 0.050 |
| D-Panthenol | D-panthenol | DSM | 0.500 | 0.500 |
| Benzyl Alcohol NF/FCC/EP/BP | Benzyl Alcohol | Emerald Performance Materials | 0.200 | 0.200 |
| Phenoxyethanol | Bornidox ® 1160 | BASF | 0.250 | 0.250 |
| 1,3-Butylene Glycol | 1,3 Butylene Glycol | KH Neochem Ltd | 2.000 | 2.000 |
| Hydrolite 5 | Pentylene Glycol | Symrise | 3.000 | 3.000 |
| Keltrol T | Xanthan gum | CP Kelco | 0.050 | 0.050 |
| Fragrance | - | P&G | 0.033 | 0.030 |
| Purac Hi Pure 90 | L- Lactic acid and Water | Corbion | | |
| Purasal S HQ-60 | Sodium L- Lactate and Water | Corbion | | |
| Rheodol TWL-120 | PEG-20 Sorbitan Cocoate | Kao Chemicals | 0.125 | |

Fig. 7B

| | | | Comparative Example I | |
|---|---|---|---|---|
| Trade Name | INCI name | Manufacturer | 1st Portion (weight %) | 2nd Portion (weight %) |
| Eldew PS-203 | Phytosteryl/Octyldodecyl Lauroyl Glutamate | Ajinomoto Co., Inc | 0.375 | |
| Trioctanoin | Triethylhexanoin | THE NISSHIN OILLIO GROUP | 0.875 | |
| Miglyol 812 | Caprylic/Capric Triglyceride. | Cremer Oleo Gmbh | 0.125 | |
| KF-6011P | PEG-11 Methyl Ether Dimethicone | Shietsu Chemicals | 0.063 | |
| Sepigel 305 | Polyacrylamide (and) C13-14 Isoparaffin (and) Laureth-7 | Seppic | 0.150 | |
| GLW65KTAP | Titanium Dioxide Water Glycerin; and Ammonium Polyacrylate | Kobo Products Inc. | 1.154 | |

Fig. 7C

|  |  |  | Comparative Example I | |
|---|---|---|---|---|
| Trade Name | INCI name | Manufacturer | 1st Portion (weight %) | 2nd Portion (weight %) |
| UNICERT RED K7057-J | FD&C RedNo.33( CI17200) | Sensient | | |
| Red 40 (CI16035) | FD&C Red No. 40 (CI16035) | Sensient | 0.006 | |
| Unicert Yellow 08005-J | FD&C Yellow No.5 (CI19140) | Sensient | 0.009 | |
| | | Total | 100.000 | 100.000 |

Fig. 7D

| Metrics | Parameter | Units | | |
|---|---|---|---|---|
| Shape related | Percent Surrounded | % | 25.6% | |
| | Crossover Stress | Pa | 29 | 38 |
| | L/H (Length/Height) | | 2.45 | |
| | Length | cm | 1.32 | |
| | Height | cm | 0.54 | |
| | Flowability (Speed) | cm/min | 0.90 | 0.60 |
| Contrast | Opacity | % | 100 | 3 |
| | L*, a*, b* | | L* = 78.85<br>a* = 22.49<br>b* = 25.37 | L* = 79.52<br>a* = -1.28<br>b* = 4.35 |
| | Delta E* | | 31.74 | |

Fig. 7E

Table 2: Formulation and Data for Inventive Example II and III

| | | EXAMPLE: | II | | III | |
|---|---|---|---|---|---|---|
| Trade Name | INCI name | Manufacturer | 1st Portion (weight %) | 2nd Portion (weight %) | 1st Portion (weight %) | 2nd Portion (weight %) |
| Purified Water | Purified Water | | QS | QS | QS | QS |
| Sepimax Zen | Polyacrylate crosspolymer | Seppic | | | 1.500 | |
| Ultrez 20 | Acrylates/C10-30 Alkyl Acrylate Crosspolymer | Lubrizol | 0.363 | 0.400 | | 0.400 |
| Aristoflex Silk | Sodium Polyacryloyldimethyl Taurate | Clariant | | | | |
| AMP Ultra PC 1000 Neutralizing amine | Aminomethyl Propanol | AngusChemie Gmbh | 0.238 | 0.240 | | 0.150 |
| Galactomyces Ferment Filtrate | Galactomyces Ferment Filtrate, Butylene Glycol and Methylparaben | P&G | | | | 13.330 |

Fig. 8A

| | | EXAMPLE: | II | | III | |
|---|---|---|---|---|---|---|
| Trade Name | INCI name | Manufacturer | 1st Portion (weight %) | 2nd Portion (weight %) | 1st Portion (weight %) | 2nd Portion (weight %) |
| Disodium EDTA | Disodium EDTA | Nagase ChemTex | 0.100 | 0.100 | 0.100 | |
| Glycerin 99% | Glycerin | P&G Chemicals | 5.000 | 5.000 | 5.000 | 5.000 |
| Xylitol C | Xylitol | Danisco | 3.000 | 3.000 | 3.000 | 3.000 |
| Niacinamide USP | Niacinamide | Western Drugs Limited | 5.000 | 5.000 | | 2.670 |
| Probenz SP Powder | Sodium Benzoate | Eastman | 0.050 | 0.050 | 0.050 | |
| D-Panthenol | D-panthenol | DSM | 0.500 | 0.500 | 0.500 | 0.500 |
| Benzyl Alcohol NF/FCC/EP/BP | Benzyl Alcohol | Emerald Performance Materials | 0.200 | 0.200 | | |
| Phenoxyethanol | Bornidox ® 1160 | BASF | 0.250 | 0.250 | 0.250 | 0.250 |
| 1,3-Butylene Glycol | 1,3 Butylene Glycol | KH Neochem Ltd | 2.000 | 2.000 | | |
| Hydrolite 5 | Pentylene Glycol | Symrise | 3.000 | 3.000 | | |
| Keltrol T | Xanthan gum | CP Kelco | 0.050 | 0.050 | | |
| Fragrance | - | P&G | 0.033 | 0.030 | 0.030 | 0.030 |

Fig. 8B

| | | EXAMPLE: | II | | III | |
|---|---|---|---|---|---|---|
| Trade Name | INCI name | Manufacturer | 1st Portion (weight %) | 2nd Portion (weight %) | 1st Portion (weight %) | 2nd Portion (weight %) |
| Purac Hi Pure 90 | L- Lactic acid and Water | Corbion | | | 3.300 | |
| Purasal S HQ-60 | Sodium L- Lactate and Water | Corbion | | | 3.000 | |
| Rheodol TWL-120 | PEG-20 Sorbitan Cocoate | Kao Chemicals | 0.125 | | | |
| Eldew PS-203 | Phytosteryl/Octyldodecyl Lauroyl Glutamate | Ajinomoto Co., Inc | 0.375 | | | |
| Trioctanoin | Triethylhexanoin | THE NISSHIN OILLIO GROUP | 0.875 | | | |
| Miglyol 812 | Caprylic/Capric Triglyceride. | Cremer Oleo Gmbh | 0.125 | | | |
| KF-6011P | PEG-11 Methyl Ether Dimethicone | Shietsu Chemicals | 0.063 | | | |
| Sepigel 305 | Polyacrylamide (and) C13-14 Isoparaffin (and) Laureth-7 | Seppic | 0.150 | | | |

Fig. 8C

| | EXAMPLE: | II | | III | |
|---|---|---|---|---|---|
| Trade Name | INCI name | Manufacturer | 1st Portion (weight %) | 2nd Portion (weight %) | 1st Portion (weight %) | 2nd Portion (weight %) |
| GLW65KTAP | Titanium Dioxide Water Glycerin & Ammonium Polyacrylate | Kobo Products Inc. | 1.154 | | | |
| UNICERT RED K7057-J | FD&C RedNo.33(CI17200) | Sensient | | | | |
| Red 40 (CI16035) | FD&C Red No. 40 (CI16035) | Sensient | 0.006 | | 0.002 | |
| Unicert Yellow 08005-J | FD&C Yellow No.5 (CI19140) | Sensient | 0.009 | | 0.003 | |
| | | Total | 100.000 | 100.000 | 100.000 | 100.000 |

Fig. 8D

| Metrics | Parameter | Units | | | |
|---|---|---|---|---|---|
| Shape related | Percent Surrounded | % | 100 | 100 | 100 |
| | Crossover Stress | Pa | 29 | 38 | 54 | 46 |
| | L/H (Length/Height) | | 2.45 | | 2.81 |
| | Length | cm | 1.32 | | 1.31 |
| | Height | cm | 0.54 | | 0.46 |
| | Flowability (Speed) | cm/min | 0.90 | 0.60 | 0.25 | 0.36 |
| | Opacity | % | 100 | 3 | 10 | 4 |
| Contrast | L*, a*, b* | | L*= 78.85  a* = 22.49  b* = 25.37 | L*= 79.52  a*= -1.28  b*= 4.35 | L*=49.92  a*= 48.22  b*=77.93 | L*= 77.42  a*=-1.18  b*= 3.95 |
| | Delta E* | | 31.74 | | 93.11 |

Fig. 8E

Table 3: Formulation and Data for Inventive Examples IV and V

| | EXAMPLE | IV | | V | |
|---|---|---|---|---|---|
| Trade Name | INCI name | Manufacturer | 1st Portion (weight %) | 2nd Portion (weight %) | 1st Portion (weight %) | 2nd Portion (weight %) |
| Purified Water | Purified Water | | QS | QS | QS | QS |
| Sepimax Zen | Polyacrylate 6 crosspolymer | Seppic | | 1.200 | | 1.500 |
| Ultrez 20 | Acrylates/C10-30 Alkyl Acrylate Crosspolymer | Lubrizol | 0.400 | | 0.400 | |
| Aristoflex Silk | Sodium Polyacryloyldimethyl Taurate | Clariant | | | | |
| AMP Ultra PC 1000 Neutraizing amine | Aminomethyl Propanol | AngusChemie Gmbh | 0.150 | | 0.150 | |
| Galactomyces Ferment Filtrate | Galactomyces Ferment Filtrate, Butylene Glycol and Methylparaben | P&G | 40.000 | | | |

Fig. 9A

| Trade Name | EXAMPLE INCI name | Manufacturer | IV 1st Portion (weight %) | IV 2nd Portion (weight %) | V 1st Portion (weight %) | V 2nd Portion (weight %) |
|---|---|---|---|---|---|---|
| Disodium EDTA | Disodium EDTA | Nagase ChemTex | 0.050 | 0.050 | 0.050 | 0.050 |
| Glycerin 99% | Glycerin | P&G Chemicals | 5.000 | 5.000 | 6.000 | 6.000 |
| Xylitol C | Xylitol | Danisco | 3.000 | 3.000 | | |
| Niacinamide USP | Niacinamide | Western Drugs Limited | 8.000 | | 2.000 | 2.000 |
| Probenz SP Powder | Sodium Benzoate | Eastman | | 0.050 | 0.050 | 0.050 |
| D-Panthenol | D-panthenol | DSM | 0.500 | 0.500 | | |
| Benzyl Alcohol NF/FCC/EP/BP | Benzyl Alcohol | Emerald Performance Materials | | | | |
| Phenoxyethanol | Bornidox ® 1160 | BASF | 0.250 | 0.250 | 0.250 | 0.250 |
| 1,3-Butylene Glycol | 1,3 Butylene Glycol | KH Neochem Ltd | | | | |
| Hydrolite 5 | Pentylene Glycol | Symrise | | | | |
| Keltrol T | Xanthan gum | CP Kelco | | | | |

Fig. 9B

| Trade Name | EXAMPLE INCI name | Manufacturer | IV 1st Portion (weight %) | IV 2nd Portion (weight %) | V 1st Portion (weight %) | V 2nd Portion (weight %) |
|---|---|---|---|---|---|---|
| Fragrance | - | P&G | 0.030 | 0.030 | 0.050 | |
| Purac Hi Pure 90 | L- Lactic acid and Water | Corbion | | | | |
| Purasal S HQ-60 | Sodium L- Lactate and Water | Corbion | | 2.200 | | |
| Rheodol TWL-120 | PEG-20 Sorbitan Cocoate | Kao Chemicals | | 2.000 | | |
| Eldew PS-203 | Phytosteryl/Octyldodecyl Lauroyl Glutamate | Ajinomoto Co., Inc | | | | |
| Trioctanoin | Triethylhexanoin | THE NISSHIN OILLIO GROUP | | | | |
| Miglyol 812 | Caprylic/Capric Triglyceride. | Cremer Oleo Gmbh | | | | |
| KF-6011P | PEG-11 Methyl Ether Dimethicone | Shietsu Chemicals | | | | |

Fig. 9C

| | EXAMPLE | IV | | V | |
|---|---|---|---|---|---|
| Trade Name | INCI name | Manufacturer | 1st Portion (weight %) | 2nd Portion (weight %) | 1st Portion (weight %) | 2nd Portion (weight %) |
| Sepigel 305 | Polyacrylamide (and) C13-14 Isoparaffin (and) Laureth-7 | Seppic | | | | |
| GLW65KTAP | Titanium Dioxide Water Glycerin & Ammonium Polyacrylate | Kobo Products Inc. | | | | 0.077 |
| UNICERT RED K7057-J | FD&C RedNo.33 (CI17200) | Sensient | | | 0.002 | |
| Red 40 (CI16035) | FD&C Red No. 40 (CI16035) | Sensient | 0.002 | | | |
| Unicert Yellow 08005-J | FD&C Yellow No.5 (CI19140) | Sensient | 0.003 | | 0.003 | |
| | | Total | 100.000 | 100.000 | 100.000 | 100.000 |

Fig. 9D

| Metrics | Parameter | Units | | | |
|---|---|---|---|---|---|
| Shape related | Percent Surrounded | % | 100 | | 100 |
| | Crossover Stress | Pa | 30 | 16 | 29 | 53 |
| | L/H (Length/Height) | | 3.61 | | 2.58 |
| | Length | cm | 1.37 | | 1.07 |
| | Height | cm | 0.38 | | 0.41 |
| | Flowability (Speed) | cm/min | 0.62 | 1.25 | 0.83 | 0.50 |
| Contrast | Opacity | % | 3 | 5 | 6 | 60 |
| | L*, a*, b* | | L*= 51.97 a*=53.28 b*= 84.87 | L*= 78.78 a*=-1.16 b*=-5.02 | L*= 36.35 a*=61.57 b*=54.79 | L*= 60.69 a*=-0.85 b*=-2.19 |
| | Delta E* | | 100.29 | | 87.95 |

Fig. 9E

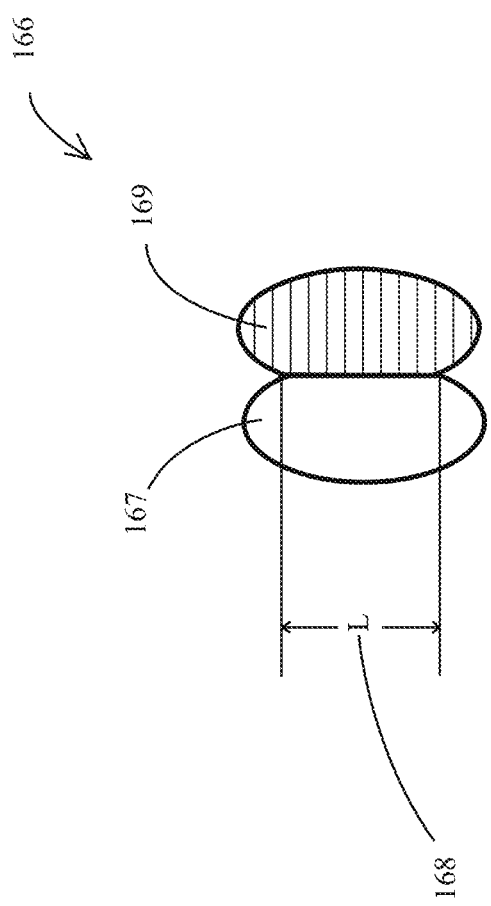

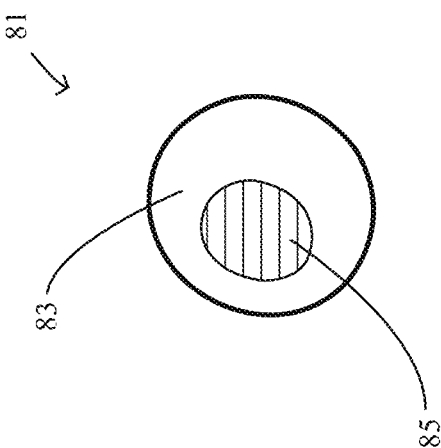
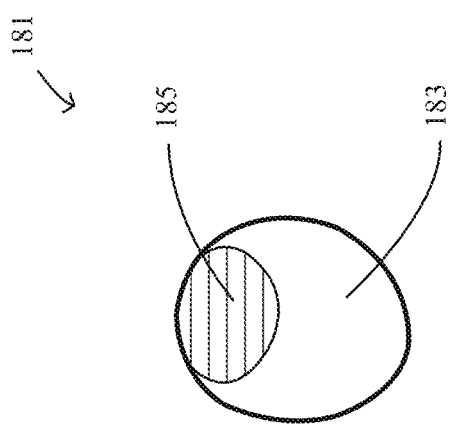

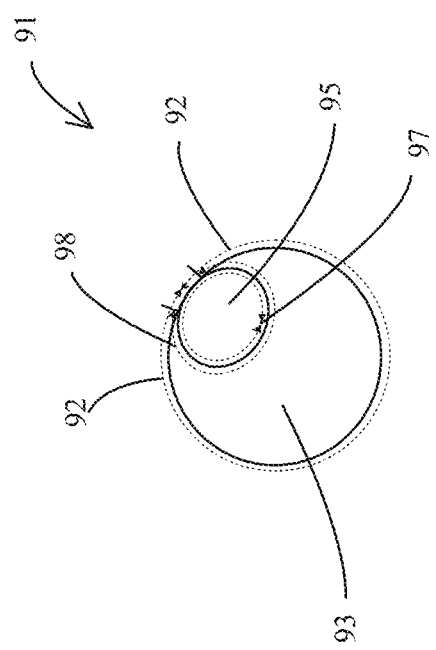

DUAL PHASE PRODUCTS

FIELD OF THE INVENTION

The present invention relates generally to dual phase products, especially suitable for personal care.

BACKGROUND OF THE INVENTION

Dual phase products are generally known. One way to dispense such products are by side-by-side dual dispensers. Such products are available in at least several consumer good categories including dental care and skin care. However, today's consumers are more discerning, especially given the myriad of choices available in the marketplace. This is particularly true in categories such as beauty care where consumers are looking for premium experience. Many of these premium experiences mimic nature. Therefore, there is a continuing need for products that not only continue to deliver benefits characteristic of the product category that consumers expect but also provide a premium experience that mimics nature.

SUMMARY OF THE INVENTION

The present invention addresses this need, at least in part, by providing a dual phase product that mimics nature while also providing the benefits consumer come to expect. One aspect of the invention provides for a discrete dispensed product comprising: a first portion; and a second portion at least partially surrounding the first portion. In some examples, the discrete dispensed product mimics roe (e.g., caviar, salmon eggs, etc.) thereby conjuring images of premium and distinct offerings. In one example, a second transparent portion partially surrounds a non-transparent first portion. In another example, the non-transparent first portion has red-orange color thereby mimicking salmon eggs.

Another aspect provides for a discrete dispensed product comprising: a first portion; and a second portion at least partially surrounds the first portion at least more than 50% of a maximum perimeter of the first portion, wherein the maximum perimeter is the perimeter defined around the largest cross-sectional area of the first portion, wherein said largest cross-sectional area is either in a plane parallel to or in the same plane as a planar contact surface of the discrete dispensed product.

Another aspect provides for a discrete dispensed product comprising: a first portion; and a second portion at least partially surrounding the first portion, wherein the second portion comprises a Crossover Stress assessed by a Portion Oscillatory Rheometry Test Method ("PORTM") as described herein, wherein the Crossover Stress of the second portion is equal to or greater than 10 Pascals (Pa).

Another aspect provides for a discrete dispensed product comprising: a first portion; and a second portion at least partially surrounding the first portion, wherein the second portion is at least partially transparent, preferably transparent.

Another aspect provides for a dispenser. The dispenser comprises a first reservoir and a second reservoir. The first reservoir contains a first composition and the second reservoir contains a second composition, wherein the second composition is a least partially transparent. The first reservoir is in fluid communication with a first fluid channel comprising a first outlet orifice. The second reservoir is in fluid communication with a second fluid channel comprising a second outlet orifice. The second outlet orifice at least partially surrounds a perimeter of the first outlet orifice.

One advantage described herein is separating incompatible ingredients between two phases. In one example, a first composition comprising a skin care active such as niacinamide, wherein the first composition is at relatively neutral pH. The neutral pH helps with shelf stability of the active. The second composition is a relatively acidic pH. When the first and second composition are dispensed, subsequently the two compositions are mixed, as a result the overall pH will lower thereby providing a pH that improves the efficacy of niacinamide in and on skin.

While the specification concludes with claims that particularly point out and distinctly claim the invention, it is believed the present invention will be better understood from the following description.

BRIEF DESCRIPTION OF THE DRAWINGS

While the specification concludes with claims particularly defining and distinctly claiming the invention, it is believed that the invention will be better understood from the following description of the accompanying figures. In the accompanying figures:

FIGS. 1A-1F are a top view of different examples of a discrete dispensed product (wherein 1F is a comparative example);

FIGS. 2A-2F are a side view of different examples of the discrete dispensed product;

FIG. 4 is a front view of a dispenser comprising a nozzle capable of dispensing a discrete dispensed product;

FIGS. 7A-7E is Table 1 of a formulation and data for comparative example I;

FIGS. 8A-8E is Table 2 of a formulation and data for inventive examples II and II;

FIGS. 9A-9E is Table 3 of a formulation and data for inventive examples IV and V;

FIG. 10A is inventive and 10B is comparative;

FIG. 11 is showing the percentage by which the second portion surrounds a maximum perimeter of the first portion of comparative sample of FIG. 10B;

FIGS. 13A and 13B are each discrete dispensed products assessed for the percentage by which the second portion surrounds a maximum perimeter of the first portion;

FIG. 14 illustrates how to calculate said percentage of the discrete dispensed product of FIG. 13B.

DETAILED DESCRIPTION OF THE INVENTION

Definitions

Figure 3:
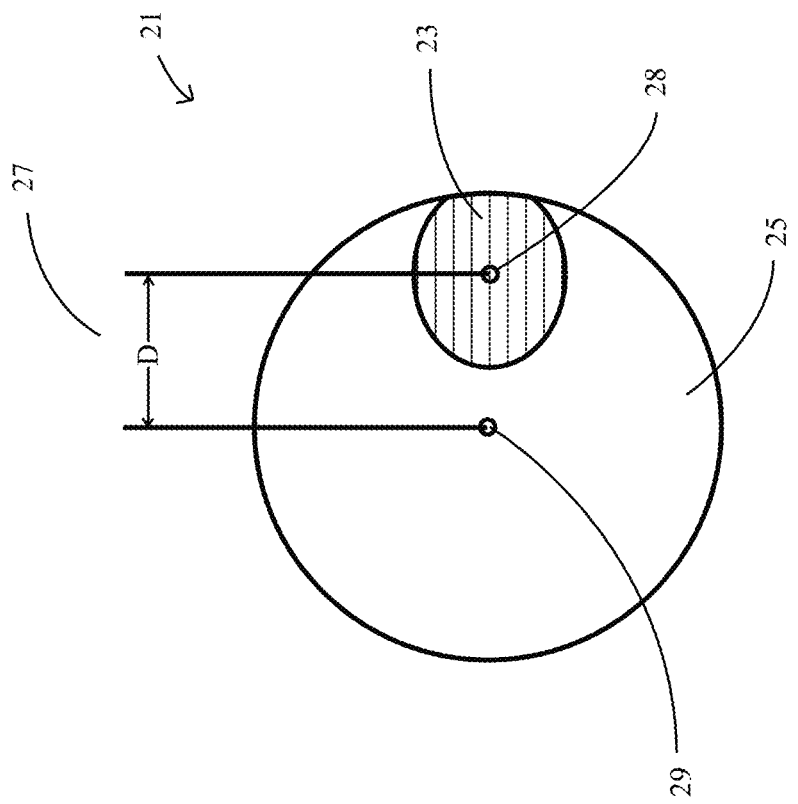
FIG. 3 is a top view measuring distance between a dispensed product center axis and a first portion center axis.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %"

herein. All molecular weights as used herein are weight average molecular weights expressed as grams/mole, unless otherwise specified.

As used herein, the articles including "a" and "an" when used in a claim, are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "oral care" means a composition, which in the ordinary course of usage, is not intentionally swallowed for purposes of systemic administration of particular therapeutic agents, but is rather retained in the oral cavity for a time sufficient to contact dental surfaces or oral tissues.

As used herein, "personal care" means a topical composition for regulating a condition of mammalian keratinous tissue (e.g., skin, hair, finger nails).

As used herein "skin care" means regulating and/or improving a skin condition. Some non-limiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

As used herein "skin care active" means a compound combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

Discrete Dispensed Product

One aspect of the invention provides a discrete dispensed product (or simply as a "dispensed product", used herein interchangeably with "discrete dispensed product"). The discrete dispensed product comprises: a first portion; and a second portion at least partially surrounding the first portion. The dispensed product is applicable, but not limited, to beauty care, personal grooming, personal cleansing, fabric care, home care, skin care, oral care, dish care, health care, baby care, feminine care, and hair care product categories. Preferably the dispensed product comprises one or more actives providing a benefit to the respective product category. For example, a dispensed fabric care product may comprise a fabric care active. Such actives may include a surfactant for fabric cleaning. Another example, a dispensed hair care product may comprise a hair care active. Such actives may include a hair conditioning active. Yet another example may include a dispensed skin care product comprising a skin care active. In yet another example, the dispensed product may be formulated as a leave-on product like a skin care moisturizing cream, or as a rinse-off product like a facial cleanser or a shampoo, or may even be formulated as a combination of leave-on and rinse-off like a hair conditioner or skin mask.

The dispensed product comprises a second portion at least partially surrounding the first portion. Preferably the second portion surrounds at least more than 50% of a maximum perimeter of the first portion, wherein the maximum perimeter is the perimeter defined around the largest cross-sectional area of the first portion, wherein said largest cross section area is either in a plane parallel to or in the same plane as a planar contact surface of the dispensed product. In turn, the planar contact surface area of the dispensed product is that portion making contact to a planar target surface. For example, the discrete dispensed product when made for a skin care application can comprise a skin care active and the planar target surface can be one or more of a human palm, backside of the palm, one of the fingers or thumb, wrist, forearm, backside of the forearm, facial skin etc. For analytical testing, for example, a planar Lenta Card may serve as the planar target surface. More preferably the second portion surrounds from 55% to 100% of the maximum perimeter of the first portion, yet more preferably 60% to 100%, yet still more preferably from 70% to 100%. Alternatively, the second portion surrounds from 60% to 95%, or from 70% to 80%, or from 51% to 65%, or from 85% to 100%, or from 90% to 98%, of the maximum perimeter of the first portion. Non-limiting percentage examples include: 55%, 60%, 65%, 70%, 75%, 80%, 90%, 95%, 98%, 99%, or 100%. These percentages may also be generally applicable to those examples wherein the second portion at least partially surrounds a third or more portions. One method of assessing the percentage of the second portion surrounding the first portion is described in the Examples section below.

FIGS. 1A-1E are a top view, schematic representation, of different examples of the discrete dispensed product (1, 201, 301, 401, 501, respectively). In FIGS. 1A-1E, the second portion (3, 203, 303, 403, 503) surrounds at least more than 50% of a maximum perimeter of the first portion (5, 205, 305, 405, 505, 605, respectively). As illustrated in FIG. 1A-1E, the size and location of the first portion can vary (relatively to the second portion). FIG. 1F a top view, schematic representation, of a comparative example of a discrete dispensed product (601). The second portion (603) and the first portion (605) are essentially next to each other as dispensed from a classic side-by-side dispenser.

Overall Shape of the Discrete Dispensed Product

Preferably the dispensed product comprises substantially hemi-spherical shape, preferably a compressed substantially hemi-spherical shape. In an example, the first portion comprises generally a substantially spheroid shape, preferably generally a substantially elongated spheroid shape. In another example, the first portion (or third or more portions) is at least partially, preferably fully suspended in the second portion.

Dimensions of the Discrete Dispensed Product

The overall dimensions, volumes, and mass of the dispensed product will depend upon the product category and the benefits provided. For the purpose of clarity, below is the description of the overall dimensions, volume and mass of an example of the dispensed product for a leave-on skin care application. However, one skilled in the art can accordingly make the dispensed product bigger or smaller depending on the application and the benefits provided by the dispensed product. Preferably for skin care application, a length of the dispensed product is from 0.5 cm to 2.5 cm, preferably from 1 cm to 2 cm, wherein the length is the longest dimension measured along a planar contact surface of the dispensed product. Non-limiting examples of length include 0.75 cm, 1.5 cm, or 2 cm. The term planar contact surface is that portion which the dispensed product contacts a planar target surface. In one example, the planar target surface is a surface in need of a treatment for application of the discrete dispensed product. For most technical assessments, a flat Leneta Card (Opacity Card Form 2A, Leneta Company, Inc, Mahwah, NJ, USA, hereafter referred to as "Leneta Card" or equivalent) may be used as the planar target surface. Preferably the dispensed product comprises a height from 0.2 cm to 2 cm, preferably from 0.5 cm to 1 cm, wherein the height is measured in a plane orthogonal to the planar contact surface of the dispensed product. Non-limiting examples of height include, 0.3 cm, 0.5 cm, or 0.7 cm. Preferably the dispensed product comprises a width from 0.5 cm to 2.5 cm, preferably from 1 cm to 2 cm width, wherein the width is measured 90 degrees relative to the length. Non-limiting examples of width include 0.8 cm, 1.5 cm, or 1.7 cm. Preferably the dispensed product has a ratio of the length to the width from 4:1 to 1:1, preferably from 3:1 to 1:1, more preferably from 2:1 to 1:1. Preferably the dispensed product has a ratio of the length to the height from 5:1 to 1:2, preferably from 3.75:1 to 0.9:1, more preferably from 3:1 to 0.9:1.

FIGS. 2A-2F are a side view, schematic representation, of different examples of the discrete dispensed product (11, 211, 311, 411, 511, 611, respectively). In FIGS. 2A-2F, the second portion (13, 213, 313, 413, 513, 613, respectively) surrounds at least more than 50% of a maximum perimeter of the first portion (15, 215, 315, 415, 515, 615). As illustrated in these figures, the size and location of the first portion can vary (relative to the second portion). FIG. 2E is an example of a dispensed product (511) having a relatively high length to height ratio whereas FIG. 2F is a dispensed product (611) having a relatively low length to height ratio.

The dimension of the first portion is described. Length of the first portion is from 0.1 cm to 2 cm, preferably 0.2 cm to 1 cm. Non-limiting examples of this length are 0.1, 0.2, 0.5, or 0.7 cm. The length of the first portion is measured as the longest dimension in a largest cross-sectional area of the first portion, wherein the largest cross-sectional area is either in a plane parallel to or in the same plane as a planar contact surface of the dispensed product. Preferably the height of the first portion, is from 0.1 cm to 1.25 cm, preferably 0.2 cm to 1 cm, wherein the height of the first portion is measured in a plane orthogonal to the planar contact surface of the dispensed product. Non-limiting examples of this height are 0.1, 0.2, 0.5, or 0.7 cm. Preferably the width of the first portion is from 0.1 cm to 1.25 cm, preferably 0.2 cm to 1 cm, wherein the width of the first portion is measured 90 degrees relative to the length of the first portion and of the largest cross-sectional area of the first portion. Non-limiting examples of this width are 0.1, 0.2, 0.5, or 0.7 cm FIG. 3 is a top view, schematic representation of a discrete dispensed product (21), the distance "D" (27) between a dispensed product center axis (29) and a first portion center axis (28) is less than 50% of the length of the discrete dispensed product (wherein said "length" is defined above). A second portion (25) surrounds at least more than 50% of a maximum perimeter of a first portion (23). The dispensed product center axis is defined. The dispensed product comprises a dispensed product centroid on a planar contact surface of the dispensed product. The dispensed product center axis extends through the dispensed product centroid and is orthogonal to the planar contact surface of the dispensed care product. The first portion center axis is defined. The first portion comprises a first portion centroid on a largest cross-sectional area of the first portion and a first portion center axis. The largest cross-sectional area is either in a plane parallel to or in the same plane as the planar contact surface of the dispensed product. The first portion center axis extends through the first portion centroid and is orthogonal to the planar contact surface of the dispensed care product. Preferably the distance between the dispensed product center axis and the first portion center axis is from is less than 40% of the length of the discrete dispensed product, preferably less than 30% of the length, more preferably less than 15% of the length. Non-limiting examples are less than 40%, less than 30%, or less than 15% of the length.

The volume and mass of the discrete dispensed product, and the first and second portions are described. The volume ratio of the first portion to the second portion is from 1:10 to 2:1, preferably 1:5 to 1:1, more preferably from 1:4 to 1:2, even more preferably 1:3. Preferably the volume of the first portion and the second portion are each independently selected from 0.05 ml to 1.5 ml, more preferably from 0.075 ml to 1.0 ml, yet still more preferably from 0.1 ml to 0.5 ml. Non-limiting examples of this volume are 0.08 ml, 0.1 ml, 0.15 ml, 0.2 ml. Preferably the total volume of the dispensed product is from 0.1 ml to 3 ml, more preferably from 0.15 ml to 2 ml, yet still more preferably from 0.2 ml to 1 ml. Non-limiting examples of this total volume are 0.1 ml, 0.2 ml, 0.3 ml, 0.4 ml, 0.5 ml, 1.5 ml, 2 ml, or 2.5 ml. The mass ratio of the first portion to the second portion is from 1:10 to 2:1, preferably 1:5 to 1:1, more preferably from 1:4 to 1:2, even more preferably 1:3. Preferably the mass of the first portion and the second portion are each independently selected from 0.05 g to 1.5 g, more preferably from 0.075 g to 1 g, yet still more preferably from 0.1 g to 0.5 g. Non-limiting examples of this mass are 0.08 g, 0.1 g, 0.15 g, 0.2 g, or 0.3 g. Preferably the total mass of the dispensed product is from 0.1 g to 3 g, more preferably from 0.15 g to 2 g, yet still more preferably from 0.2 g to 1 g. Non-limiting examples of this total mass are 0.1 g, 0.2 g, 0.3 g, 0.4 g, 0.5 g, 0.7 g, 1 g, 1.5 g, 1.7 g, or 1.9 g.

In one example, the discrete dispensed product is a shampoo, wherein the total mass is from 3 g to 15 g, preferably from 9 g to 13g. In another example the discrete dispensed product is a skin care mask, wherein the total mass is from 5 g to 15 g, preferably from 8 g to 12 g. In another example, the discrete dispensed product is an oral care product, wherein the total mass is from 1 g to 3 g, preferably the oral care product is a dentifrice.

Ingredients

Formulary ingredients of the first and second compositions are described. Many of the examples are for skin care applications. However, one skilled in the art can appropriately formulate the first and second compositions depending on the product focus area. These ingredients include structuring agents, gel networks, colorants, opacifiers, and preferred actives. Although the terms "first composition" and "second composition" are used, the terms "first portion" and "second portion" are interchangeable, respectively.

Structuring Agents

The first and second compositions of the present invention may comprise structuring agents, which may be used to increase viscosity, thicken, solidify, or provide solid or crystalline structure to the compositions. Structuring agents are typically grouped based on solubility, dispersibility, or phase compatibility. Examples of aqueous or water structuring agents include polymeric agents, natural or synthetic gums, polysaccharides, and the like. Suitable classes of structuring agents include but are not limited to carboxylic acid polymers, polyacrylamide polymers, sulfonated polymers, copolymers thereof, hydrophobically modified derivatives thereof, gums, celluloses, superabsorbent polymers, and mixtures thereof. For example, each composition may independently comprise from 0.0001%, 0.001%, 0.01%, 0.05%, 0.1%, 0.5%, 1%, 2%, 3%, 5% to 25%, 20%, 10%, 7%, 5%, 4%, or 2%, by weight of the respective composition, of one or more structuring agents. Suitable polysaccharides include alkyl hydroxyalkyl cellulose ethers, such as Hydroxypropylmethylcellulose Stearoxy Ether. This material is sold under the tradename of Sangelose 60L and 90L from Daido Chemical Corp. Suitable polymers include crosslinked polyacrylates, such as, for example, Polyacrylate 6 Crosspolymer, sold under the tradename of Sepimax Zen, from Seppic. Another polymer includes crosslinked polymers, the monomers of which are at least partially composed of acryloyldimethyltaurate monomers, such as, for example Sodium Polyacryloyldimethyl Taurate, sold under the tradename of Aristoflex Silk, from Clariant.

The term "superabsorbent polymer" is understood to mean a polymer which is capable, in its dry state, of spontaneously absorbing at least 20 times its own weight of aqueous fluid, in particular of water and especially of distilled water.

Examples of oil structuring agents include silicone and organic based materials. Suitable ranges of oil structuring agents are from 0.01%, 0.05%, 0.1% 0.5%, 1%, 2.5%, 5%, or 10% to 30%, 25%, 20%, 15%, 10%, or 5%. Suitable oil phase structuring agents may be silicone based, such as silicone elastomers, silicone gums, silicone waxes, linear silicones having a degree of polymerization allowing the silicone to increase the viscosity of the oil phase. Examples of silicone structuring agents include, but are not limited to, silicone elastomers, silicone gums, and silicone waxes.

In some examples, the first composition or the second composition may each have a relatively high-level of water. In such examples, the second composition may comprise at least 60%, preferably from 70% to 90% more preferably from 75% to 85% water, by weight of the second composition. In another example, the first compositions may comprise at least 60%, preferably from 70% to 90% more preferably from 75% to 85% water, by weight of the second composition. In yet another example, it is both the first and second compositions that have such relatively high-levels of water.

Further details of structuring agents are described in U.S. Pat. No. 9,271,912 B2, from col. 47, line 28 to col. 51, line 49.

Gel Networks

The compositions herein may each independently comprise a gel-network. The "gel-network" is comprised of a hydrophobic structuring agent and a non-ionic, hydrophilic surfactant. Preferred levels of these individual components are specified below, however the total gel-network portion of the composition is limited separately from its individual components. Preferred compositions comprise from 1% to 20%, more preferably from 1% to 10%, most preferably from 2% to 9%, of the total one or more structuring agents and non-ionic hydrophilic surfactant by weight of the respective composition.

Preferably each composition comprises no more than 10 weight percent, and more preferably no more than 5 weight percent, of a hydrophobic, structuring agent selected from the group consisting of saturated C16 to C30 fatty alcohols, saturated C16 to C30 fatty alcohols containing from about 1 to about 5 moles of ethylene oxide, saturated C16 to C30diols, saturated C16 to C30 monoglycerol ethers, saturated C16 to C30 hydroxy fatty acids, and mixtures thereof, having a melting point of at least about 40 deg. C, Preferably each composition comprises at least 0.5 weight percent, more preferably at least 1 weight percent, even more preferably at least 2 weight percent, and still more preferably at least 3 weight percent, of a hydrophobic, structuring agent selected from the group consisting of saturated C16 to C30 fatty alcohols, saturated C16 to C30 fatty alcohols containing from about 1 to about 5 moles of ethylene oxide, saturated C16 to C30 diols, saturated C16 to C30 monoglycerol ethers, saturated C16 to C30 hydroxy fatty acids, and mixtures thereof, having a melting point of at least about 40 deg. C. Without wishing to be limited by theory, it is believed that these structuring agents are useful to assist in the formation of the theological characteristic of the composition which contribute to the hydrolytic stability of the composition of the present invention. In particular, structuring agents assist in the formation of the liquid crystalline gel network structures.

The preferred structuring agents of the present invention are selected from the group consisting of stearyl alcohol, cetyl alcohol, behenyl alcohol, stearic acid, palmitic acid, the polyethylene glycol ether of stearyl alcohol having an average of 1 to 5 ethylene oxide units, the polyethylene glycol ether of cetyl alcohol having an average of 1 to 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from the group consisting of stearyl alcohol, cetyl alcohol, behenyl alcohol, steareth-2, and mixtures thereof.

The hydrophilic surfactant is described. The compositions of the present invention comprise no more than 2% weight percent, preferably no more than 1% weight percent, and more preferably no more than 0.5% of at least one hydrophilic surfactant. Without being limited by theory, it is believed that the hydrophilic surfactant disperses the hydrophobic materials, i.e. the structuring agent, in the water phase. The surfactant, at a minimum, must be hydrophilic enough to disperse in water.

The exact surfactant chosen will depend upon the pH of the composition and the other components present. Preferred for use herein are nonionic surfactants. Among the nonionic surfactants that are useful herein are those that can be broadly defined as condensation products of long chain alcohols, e.g. C8-30 alcohols, with sugar or starch polymers, i.e., glycosides. Commercially available examples of these surfactants include decyl polyglucoside (available as APG 325 CS from Henkel) and lauryl polyglucoside (available as APG 600 CS and 625 CS from Henkel). Other useful non-ionic surfactants may include the condensation products of sorbitol with a fatty acid, Nonlimiting examples include the Tweens, Spans, and the Polysorbates. Other useful nonionic surfactants may include: condensation products of alkylene oxides with fatty acids (i.e. alkylene oxide esters of fatty acids); condensation products of alkylene oxides with 2 moles of fatty acids (i.e. alkylene oxide diesters of fatty acids); condensation products of alkylene oxides with fatty alcohols (i.e. alkylene oxide ethers of fatty alcohols); condensation products of alkylene oxides with both fatty acids and fatty alcohols, i.e. wherein the polyalkylene oxide portion is esterified on one end with a fatty acid and etherified (connected via an ether linkage) on the other end with a fatty alcohol; and polyhydroxy fatty acid amide surfactants. Non-limiting examples of other nonionic surfactants may include steareth-21, ceteareth-20, ceteareth-12, Tween-60, Tween-80, sucrose cocoate, steareth-100, PEG-100 stearate, PEG-1000 stearate, and mixtures thereof.

In one example, the first composition and the second composition each independently comprise a structuring agent, gel net-work, and combinations thereof; preferably a structuring agent; more preferably the first and second compositions each comprise a structuring agent. Preferably the structuring agent is selected from an alkyl hydroxyalkyl cellulose ether, cross linked polyacrylate, cross linked polymer comprising an acryloyldimethyltaurate as a monomer, and combinations thereof.

Visually Distinctive Portions

Preferably the first and second compositions provide respective first and second portions that are visually distinctive from each other. The use of colorants and opacifiers are described to provide this effect. Preferably at least the first composition comprises such colorants or opacifiers (wherein more preferably the second composition is at least partially transparent, even more preferably transparent). In one example, the second composition is free of colorants and opacifiers.

The color and opacity may be provided by one or more opacifying particulate materials and/or one or more colorants. Exemplary opacifying particulate materials include titanium dioxide, zinc oxide, zirconium dioxide, and the like. Titanium dioxide is a particularly suitable opacifying particulate material.

Non-limiting classes of suitable colorants include, but are not limited to organic and/or inorganic pigments, micas, pearlescent agents interference pigments, natural and/or synthetic dyes (including, for example, water-soluble, non-soluble, oil-soluble), carmines, natural colorants, lakes, including FD&C and/or D&C lakes and blends, and combination of any of the foregoing.

Additional non-limiting examples of suitable colorants include iron oxides, ferric ammonium ferrocyanide, manganese violet, ultramarine blue, and chromium oxide, phthalocyanine blue and green pigment, encapsulated dyes, and mixtures thereof. Preferred dyes include Red No. 40 and 33, and Yellow No. 5. The presence of Mica is also preferred.

Skin Care Product

In a preferred example, the discrete dispensed product is a dispensed skin care product. Accordingly, the first or second composition herein may comprise one or more of the following ingredients from these functional classes including: abrasives, absorbents, fragrances, anti-acne agents, anti-caking agents, antifoaming agents, antimicrobial agents, antifungal agents, antioxidants, binders, buffering agents, bulking agents, chelating agents, colorants, cosmetic astringents, cosmetic biocides, denaturants, drug astringents, external analgesics, film formers, opacifying agents, pH adjusters, plant derivatives, plant extracts, plant tissue extracts, plant seed extracts, plant oils, botanicals, botanical extracts, preservatives, propellants, reducing agents, sebum control agents, sequestrants, skin bleaching agents, skin-conditioning agents (e.g. humectants and occlusive agents), and skin protectants. Particularly preferred skin care actives include Vitamine B3 compounds (e.g., niacinamide) and galactorrtyces ferment filtrate (INCI: Galactomyces Ferment Filtrate; e.g., PITERA (Registered trademark). SK-II Pitera available from Kashiwayama. Skin care active are described in US 2016/0374933 A1, paragraphs 81-104. For example, each composition may independently comprise from 0.0001%, 0.001%, 0.01%, 0.05%, 0.1%, 0.5%, 1%, 2%, 3%, 5%, 50%, 80%, 95% to 50%, 25%, 20%, 10%, 7%, 5%, 4%, or 2%, by weight of the respective composition, of one or more ingredients.

Incompatible Ingredients

Examples may include separating incompatible ingredients into the respective first and second composition to help with stability but are combined, when dosed, to provide benefits.

Generally, these reactions may include separating reactants involved in Maillard reactions, reduction-oxidation reactions, undesired viscosity modification from salt and polymer reactions, catalysis, pH dependent actives, endothermic reactions, exothermic reactions, hydrophilic vs. hydrophilic phases interactions, color shifts, and the like. A preferred example of separating incompatible ingredients includes separating certain vitamins and pro-vitamins (e.g., niacinamide) from lower pH conditions to help stop degradation. Thus, one composition comprises the vitamin/pro-vitamin under relatively neutral pH while the other composition is a relatively lower pH. This will help with shelf stability of the vitamin/pro-vitamin Upon dosing the compositions to form the discrete dispensed composition, the vitamin/pro-vitamin are able to interact with the lower pH composition. For example, it is reported that niacinamide's technical benefit dramatically increases when delivered at lower pH. In one example, one composition is at or below pH 5, while the other composition is above pH 5; preferably the one composition has a pH from 2.5 to 5, or 3 to 4, while the other composition has a pH from above 5 to 8, or from 5.5 to 7. In another example, the difference between the pH of the two compositions is at least a 1 pH value, or at least a 2 pH value, or at least a 3 pH value.

In one example, the discrete dispensed product comprises either: (i) the first portion comprises a vitamin or pro-vitamin, and the second portion comprises a pH lower than the first composition; or (ii) the second portion comprises a vitamin or pro-vitamin, and the first portion comprises a pH lower than the second portion. Preferably wherein the vitamin or pro-vitamin comprises a niacinamide. More preferably wherein the first or second portion comprising the vitamin or pro-vitamin comprises a pH above 5, preferably above 5 to 8. Yet more preferably wherein the second or first portion comprising a pH lower than first and second portion respectively, comprises a pH at or below pH 5, preferably from 2.5 to 5.

One skilled in the art of making skin care formulations will appreciate that suitable pH modifiers may be used for achieving the desired pH of the first and second composition. For example, for lowering the pH (i e making the composition more acidic), one may use acidic pH modifiers such as hydroxy acid, citric acid, lactic acid, malic acid, beta hydro acid, salicylic acid, lactobionic acids, gluconic acids, acetyl and inorganic acids. Preferred acidic pH modifiers may include lactic acid, gluconic acid, or combination thereof. For example, for increasing the pH (i.e. making the composition more basic) one may use basic pH modifiers like TEA (trimethylamine), NaOH, or combination thereof.

Rheological Properties

Rheological properties of Flowability and Crossover Stress of the first portion and the second portion of the discrete dispensed product are described. The speed of the first portion and the second portion is assessed by a Discrete Dispensed Product Flowability Test Method ("DDPFTM")

as described in the Examples section below. Preferably this speed for either of the second product or the first product is from 0 cm/minute to 4 cm/minute, preferably from 0 to 3 cm/minute, more preferably from 0 to 2.25 cm/minute, even more preferably from 0 to 1 cm/minute (cm/min). Non-limiting examples of the speed are 0.5, 0.8, 1, 1.5, 2, or 2.25 cm/min. One advantage of a discrete dispensed product comprising the first and second portion having such low speeds is that this helps the dispensed product to substantially retain its dispensed shape after being dispensed. In one example, the speed ratio between the second portion and the first portion is from 4:1 to 1:4, preferably from 3:1 to 1:3, more preferably from 2:1 to 1:2. Non-limiting examples of this speed ratio include: 3:1, 2:1, 1:1, or 1:2.

Crossover Stress is described. Each portion (first portion or second portion), of the discrete dispensed product, comprises a Crossover Stress assessed by a Portion Oscillatory Rheometry Test Method ("PORTM") as described in the Examples section below. Preferably the second portion comprises a Crossover Stress which is equal to or greater than 10 Pascals (Pa), preferably from 10 Pa to 120 Pa, more preferably from 10 to 80 Pa, even more preferably from 15 to 50 Pa. Non-limiting examples of the Crossover Stress of the second portion is from 15, 25, or 40 Pa. Preferably the first portion comprises a Crossover Stress, assessed by PORTM, equal to or greater than 5 Pa, preferably from 5 to 120 Pa, more preferably from 5 to 80 Pa, even more preferably from 10 to 50 Pa. Non-limiting examples of the Crossover Stress of the first portion is from 15, 25, or 40 Pa. One advantage of a second portion having such a Crossover Stress is that the discrete dispensed product substantially retains its dispensed shape after being dispensed. Another advantage of a second portion having such a Crossover Stress is that the first portion remains distinct within the dispensed product. One advantage of a first portion having such a Crossover Stress is that the discrete dispensed product substantially retains its dispensed shape after being dispensed.

In one example, the Crossover Stress ratio between the second portion and the first portion is from 4:1 to 1:4, preferably from 3:1 to 1:3, more preferably from 2:1 to 1:2. Non-limiting examples of this Crossover Stress ratio include: 1:3, 1:2, 1:1, or 2:1. Although first and second portions are described, the method would of course also apply to the first and second compositions.

Contrast

Contrast properties of Opacity Percentage and Delta E* value are described. Each portion, of the discrete dispensed product, comprises an Opacity Percentage assessed by a Portion Opacity Test Method ("POTM") as described in the Examples section below. Preferably the first portion comprises an Opacity Percentage from 100% to 0%, preferably from 90% to 0%, more preferably 60% to 0%. Non-limiting examples of this Opacity Percentage of the first portion is 50%, 60%, 70%, or 80%. Preferably the second portion comprises an Opacity Percentage, assessed by POTM, from 0% to 90%, preferably from 0% to 80%, more preferably from 0% to 60%, yet more preferably from 0% to 10%. Non-limiting examples of this Opacity Percentage of the second portion is 5%, 10%, 15%, 20%, 25%. One advantage of the Opacity Percentage values described is that the first portion remains visually distinct from a partially transparent second portion. Thus, providing further distinct and premium dispensed product appearance.

In one example, the first portion has a higher Opacity Percentage than the second portion wherein, the difference between the first and second portions is 15% to 100%, preferably from 25% to 100%, more preferably from 50% to 100%. Non-limiting examples of this Opacity Percentage difference between the first and second portion is 40%, 50%, 60%, 70%, 80%, or 90%. One advantage of a high Opacity Percentage difference between the first and second portions is that the portions remain distinct even without large Delta E* between the portions.

The first portion and the second portion, of the discrete dispensed product, comprises a Delta E* value assessed by a Portion Delta E* Test Method ("PDETM") as described in the Examples section below. Preferably this Delta E* value is greater than 5, preferably greater than 35, more preferably from 35 to 200, even more preferably 35 to 150, even further preferably 50 to 120. Non-limiting examples of this Delta E* value is 30, 50, 60, 70, 80, 90, 100, 110. One advantage of the Delta E* values described is in providing enhanced noticeability between the first portion and second portion.

In one example, the second portion of dispensed product is at least partially transparent, preferably transparent. As used herein, "transparent" means having the property of transmitting light without appreciable scattering so that bodies lying beyond are seen clearly. Preferably the first portion is not transparent, preferably the first portion is opaque, more preferably opaque and having a colorant. Preferably the colorant is selected from red, yellow, orange, pink, or combinations thereof. One advantage of this example is it resembles premium Japanese Ikura to some consumers.

Dispenser

Examples of dispensing systems, preferably dual dispensing systems, compatible with this invention include (but are not limited to) dual chamber tubes or bottles or airless chambers having a collapsible reservoir using a collapsible wall (either a delaminating bottle or a piston) or chambers using a dip tube to draw products or a combination thereof. Referring to FIG. 4, the dispenser (31) comprising a first reservoir (37) and a second reservoir (39). The first reservoir (37) contains a first composition (not shown) and the second reservoir (39) contains a second composition (not shown). Preferably the first and the second composition is at least partially transparent, more preferably transparent. The first reservoir is in fluid communication with a first fluid channel comprising a first outlet orifice, and the second reservoir is in fluid communication with a second fluid channel comprising a second outlet orifice. The second outlet orifice at least partially surrounds a perimeter of the first outlet orifice. The first and second outlet orifices are positioned in a nozzle (41). Referring to FIG. 4, the dispenser (31) is configured to dispense a discrete dispensed product via the nozzle (41). Cross sectional views of different nozzles are provided in FIGS. 5A-5D (discussed in further detail below).

Dispensing the first composition provides the first portion and dispensing the second composition provides the second portion. These compositions are dispensed from the dispenser concurrently, or substantially concurrently, to provide the discrete dispensed product. The dispenser may have a first pump associated with the first reservoir and a second pump associated with the second reservoir. Both pumps are preferably actuatable together by means of a single pushbutton. Referring to FIG. 4, an example of this pushbutton (35) is shown at the top of the dispenser (31). The pushbutton operatively connects to the actuation rods. Total volumes/masses that the dispenser is capable of dispensing in one actuating hand movement may include those as previously described for the discrete dispensed product. The pumps may be configured to dispense different volumes of the respective first and second compositions when actuated to the end-of-stroke, by having different start/finish times, flow rates, or displacement, relative to each other. Nevertheless, preferably the actuating forces of the two actuating rods are substantially or completely identical. In one example, WO 2017/042492 A1 describes a dual dispenser characterized in that the first and second pumps comprise respective actuation rods which are axially movable with strokes of different lengths, i.e. a first actuation rod with a long stroke and a second actuation rod with a short stroke. As such, the different amounts of the respective compositions are dispensed. In one example, the first pump is a dip-tube type pump and second pump is an airless type pump. In another example, both the first and second pump are either dip-tube type or airless type pump. In yet another example, the first pump is an airless type pump and the second pump is a dip-tube type pump. In a preferred example, the pumps are actuatable by pushbutton providing the energy required for expelling the first and second compositions from the respective reservoirs. That is, the dual dispenser is hand driven. The user should be encouraged to dispense the pump with a full stroke for best results. This may be achieved by means of usage instructions, using feedback mechanism (such as visual, sound, tactile) as well as keeping the force to actuate sufficiently low. Preferably the peak force to actuate the pump(s) should be below 45N, more preferably below 35N and even more preferably below 25N; alternatively, from 45N to 10N. Non-limiting example of the peak force include 15N, 17N, 20N, 23N, 25N, or 27N.

The outlet channels are positioned together in a single nozzle. The nozzle is the exterior portion of the converged outlet channels. It is highly preferred that the first and second composition only come in contact until after exiting each other's respective first and second outlet orifices. Accordingly, it is preferred that the first outlet orifice and the second outlet orifice are co-planar. This helps to minimize risk of pre-mature cross-contamination of the first and second composition during dosing.

Figure 5B:
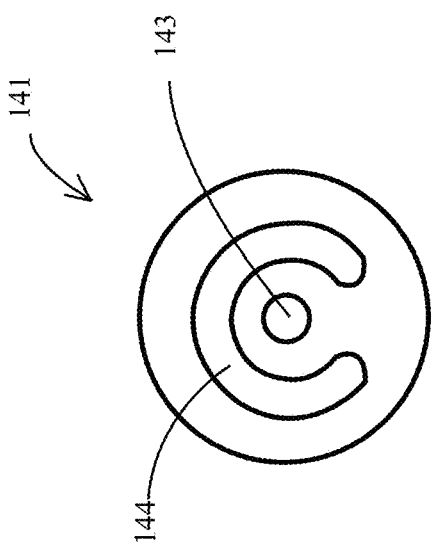
FIGS. 5A-5D are each a cross sectional view of nozzle examples that may be used with the dispenser of FIG. 4
Figure 5A:
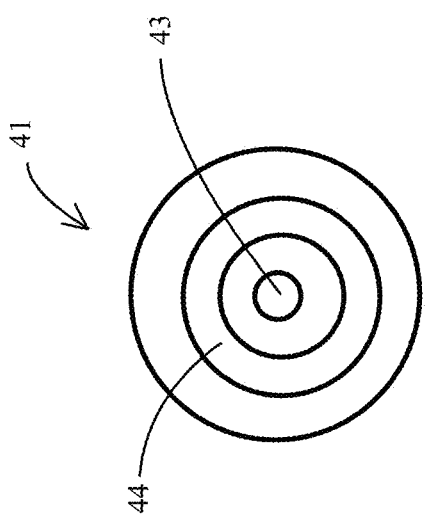

Turning to FIGS. 5A-5D, cross sectional view of various nozzles (41, 141, 241, 341, respectively). A first outlet orifice of the FIG. 5A-51D (43, 143, 243, 343, respectively) is centrally located. A second outlet orifice of FIG. 5A-5D (44, 144, 244, 344, respectively) at least partially surrounds a perimeter of the first outlet orifice. In FIG. 5A, the second outlet orifice completely surrounds the perimeter of the first outlet orifice, i.e., the second outlet orifice concentrically surrounds the first outlet orifice. In FIG. 5B, the second outlet orifice does not completely surround the first outlet. FIG. 6 is the same cross section view of nozzle of FIG. 5B but indicates angle Theta (57) to describe the percentage that the second outlet orifice (54) surrounds the perimeter of the first outlet orifice (53). A central axis (56) intersect the centroid of the first outlet orifice and is perpendicular to the cross-sectional plane. Angle Theta is measured around the central axis (56). In FIG. 6 (and thus by analogy to FIG. 5B) the second outlet orifice (54) surrounds 88% of the perimeter of the first outlet orifice (53). Applying this same approach to FIG. 5C, the second outlet orifice (244) surrounds 50% of the perimeter of the first outlet orifice (243). In one example, the second outlet orifice at least partially surrounds 25%, preferably at least 40% of a perimeter of the first outlet orifice. Non-limiting examples of this percentage may include:

10%, 25%, 40%, 60%, 80%, or 90%.

Figure 5D:
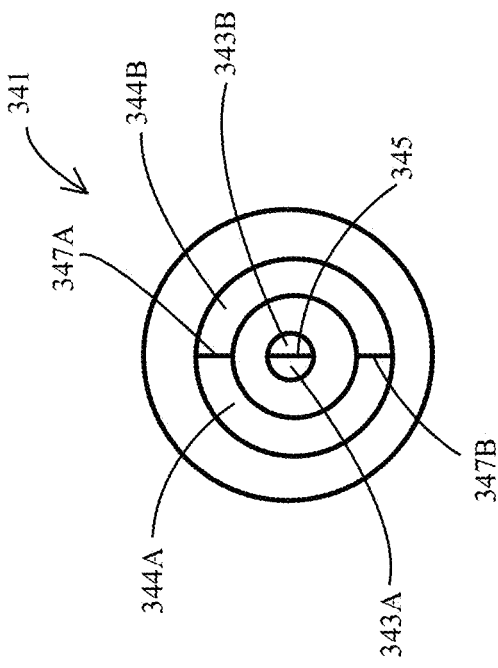
Figure 5C:
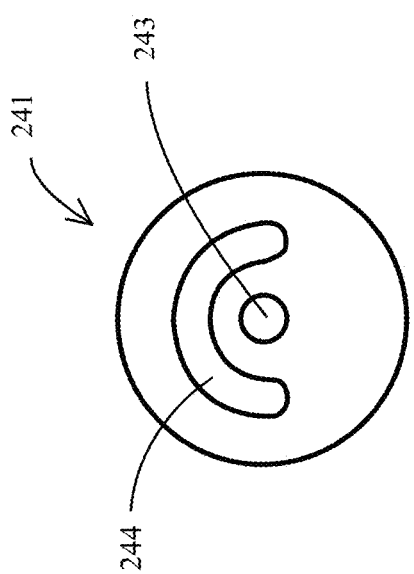
Figure 6:
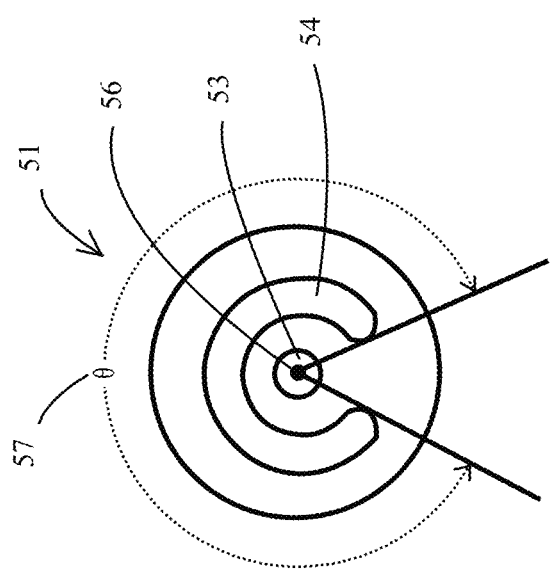
FIG. 6 is a cross section view of a nozzle showing the percentage that a second orifice is surrounding a first orifice.

FIG. 5D is cross sectional view of a nozzle (341) that is analogous to FIG. 5A except for the presence of septa (345, 347A, 347B). An outer top septum (347A) and an outer bottom septum (347B) divides the second outlet orifice into equally dimensioned left second outlet orifice (344A) and right second outlet orifice (344B). The left and right second outlet orifices together (344A, 344B) completely surrounds (save for the presence of the septa (347)) a perimeter of the first outlet orifice (343A, 343B). The first outlet orifice is also divided by an inner septum (345) into equally dimensioned left first outlet orifice (343A) and a right first outlet orifice (343B). The septum may provide advantages including: greater stability into the first outlet orifice, particularly when dispensing larger volumes of dispensed product; or providing unique structure/shape to the discrete dispensed product. In one example, a septum divides: the first outlet orifice; or at least partially the second outlet orifice; or both first outlet orifice and at least partially the second outlet orifice.

Varying the cross sectional area of the inner first orifice(s) and the surrounding second orifice(s) may influence the level of post-dispense drooling and the force to actuate. If the cross-sectional area of one channel becomes too low, the force to actuate may increase excessively. Conversely if the cross sectional area is too large, the product appearance may start to be less consistent as well as the user may experience a significant amount of post dispense drooling. Controlling for other variables of dispensing (using, for example, the controlled dosing method describe in the Examples section, the total cross section area of the inner orifice(s) is from 1 $mm^2$ to 5 $mm^2$, or from 2-3.5 $mm^2$. The total cross section area of the outer surrounding orifices(s) is from 10 $mm^2$ to 50 $mm^2$, or from 20 $mm^2$ to 40 $mm^2$, or from 25 $mm^2$ to 37 $mm^2$, or from 29 $mm^2$ to 35 $mm^2$. In one example, reference FIG. 5A, the total cross section area of the inner office (43) is 2.78 $mm^2$ and the outer surrounding orifice (44) is 31.72 $mm^2$.

Without wishing to be bound by the theory, we have found that the best dispensing results when the cross section of the first and second outlet orifices are optimized such that the flow rate from each outlet orifices is similar. This ensures simultaneous dispensing of the first and second compositions. For example, it's preferred that each outlet orifice has a similar cross section when: the first and second composition to be dispensed have comparable flow viscosities; the dispensing fluid channels provide similar resistance; and the dispenser acts on valves of similar stroke/dosage. However, to achieve some of the aesthetics described in the examples, it may be advantageous to use a different ratio of the respective outlet cross sectional area. This is because sometimes it is preferable to phase out the flow emerging from each dispensing channel, possibly even using a different pump ratio. In one example, the ratio between a cross sectional area of the first outlet orifice and a cross sectional area of the second outlet orifice is from 1:5 to 1:20, preferably from 1:8 to 1:15, more preferably 1:9 to 1:13. Preferably the dual dispenser is a skin care dual dispenser.

EXAMPLES

Formulation Examples

FIGS. 7A-7E is Table 1 of a formulation and data for comparative example I1. FIGS. 8A-8E is Table 2 of a formulation and data for inventive examples II and II. FIGS. 9A-9E is Table 3 of a formulation and data for inventive examples IV and V. All portions ingredients are mixed together until homogeneous and uniform (no visible lumps) composition is obtained. In those first or second portions containing Acrylates/C10-30 alkyl acrylate crosspolymer, neutralization with Aminomethyl Propanol is carried out followed by addition of all other ingredients while mixing until a homogeneous and uniform composition is obtained. All measurements are done on 0.30 g of discrete dispensed product weighed by Mettler Toledo New Classic MF (Model: MS4002S/01). Measurements are done in triplicate and the arithmetic mean is reported.

Consumer Preference

A 30-member consumer panel is used to assess the visual preference between a comparative "side-by-side" dispensed product and an example of the present invention. FIG. 10A is a top view, schematic representation, of the dispensed product (61) of inventive Example A. The second portion (63) surrounds the first portion (65). A cross sectional view of the nozzle used to dispense inventive Example A is previously described at FIG. 5A. For inventive Example A, Neomix package with concentric nozzle design available from Aptar supplier is used, which dispenses a total volume of 0.3 ml (~0.3 gram) in a volume ratio between the first portion and the second portion of 1:3 (i.e. 1 part of the first portion and 3 parts of the second portion). Notably, as can be seen with a naked eye, in the inventive Example A, the second portion fully surrounds the first portion.

Figure 10B:
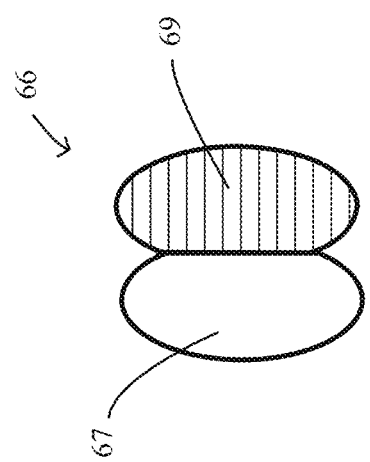
FIGS. 10A-10B are samples from a consumer preference study.
Figure 10A:
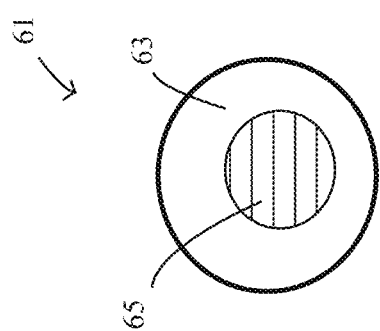
Figure 12:
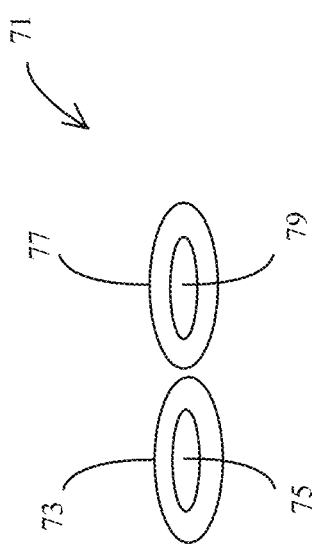
FIG. 12 is a cross section view of a side-by-side nozzle that is used to make the comparative sample of FIG. 10B.

FIG. 10B is a top view, schematic representation, of the dispensed product (66) of comparative Example B. The second portion (67) is abutting the first portion (69). FIG. 11 is also a top view, schematic representation of the dispensed product (166) of comparative Example B, and is analogous to the dispensed product FIG. 10B; however, a length (L) of the abutment (168) between the first portion (169) and second portion (167) is shown. The length (L) of abutment (168) is used to calculate percentage that which the second portion (167) surrounds a maximum perimeter of the first portion (169) as defined below in "Percentage Surrounding" method. Referencing FIG. 12, a "side-by-side" nozzle (71) is used to dispense the dispensed product of comparative Example B. The nozzle (71) has a first fluid channel (77) having a first outlet orifice (79) and a second fluid channel (73) having a second outlet orifice (75). The first and second fluid channels (73, 77) are side-by-side to each other. For comparative Example B, a dual chamber side-by-side dispensing package available from Yonwoo (South Korea) supplier is used, which dispenses a total volume of 0.3 ml (~0.3 gram) of discrete dispensed product in a volume ratio between the first portion and the second portion of 1:1. The formulations of the first and second portions of the respective dispensed products are the same. The formulation and data for Comparative Example B is provided in as Comparative Example I in Table 1, FIGS. 7A to 7E. And the formulation and data for Inventive Example A is provided as Example II in Table 2, FIGS. 8A to 8E.

In this assessment, panelists are asked to rate on a 0-10 scale. Higher numbers indicate greater agreement with the posed question. Statistical analysis was conducted using a two-tailed Student's t-Test where significantly different is determined when probability<0.1. Results are provided in Table 4. Inventive Example A is significantly better compared to Comparative Example B for both question posed

TABLE 4

Consumer preference of 30 panelists of inventive example A v. comparative example B.

| Question: | Inventive A | Comparative B |
|---|---|---|
| How Distinct does the product look? | 7.2 sig | 6.2 |
| How Premium does the product look? | 7.1 sig | 6.2 |

In summary, the consumer panels viewed the inventive example A as both more premium and distinctive relative to the comparative example B.

Percentage Surrounding

A test method is described to assesses the percentage that a second portion surrounds a maximum perimeter of a first portion. Results from two examples, illustrated in FIG. 13A and FIG. 13B, are provided. Both FIGS. 13A and 13B are each a top view, schematic representation of a dispensed product. FIG. 13A illustrates a discrete dispensed product (81) wherein the second portion (83) completely surrounds the first portion (85). FIG. 13B is illustrates a discrete dispensed product (181) wherein the second portion (183) does not completely surround the first portion (185) (but rather at least partially). This method assesses the percentage by which the second portion surrounds the maximum perimeter of the first portion.

In the method the subject dispensed product is dispensed on a flat Leneta Card as the planar target surface. After dispensing, a color digital image is immediately taken (preferably within 5 seconds), wherein the camera lens of camera is positioned orthogonally 20 to 30 cm away from the Leneta Card. Through image analysis, that portion of the image corresponding to the dispensed product is isolated. A threshold-based on color difference is established, and the image is partitioned into regions corresponding to the first portion (or other portions, if there are more than one portions at least partially surrounded by the second portion) and dispensed product as a whole. The percentage of the second portion surrounding the maximum perimeter of the first portion is then determined.

The dispensed product is dispensed from its dispenser, wherein the nozzle of the dispenser is directed perpendicular and remains stationary during dispensing, to the Leneta Card. In the example herein, a standardized dispenser ("electronic syringe pump" as described below) is used. Variability from nozzle movement, nozzle angle, and dispensing flow rate are standardized in the samples assessed. Inventive Formulation Example V (provided in Table 3, FIGS. 9A-9E) is assessed with two nozzles having different configurations represented by FIGS. 5A and 5B. The first portion is described as the first composition of Example V and the second portion is described as the second composition of Example V. A first syringe contains the first composition and a second syringe contains the second composition. The syringes are fluidly connected to a nozzle via flexible tubes. Briefly, the nozzle used for dispensing the dispensed product of FIG. 13A is pictorially represented in FIG. 5A where the first portion dispensing cross sectional area (i.e., first outlet orifice) is 3 $mm^2$ and the second portion dispensing cross section area (i.e., second outlet orifice) is 32 $mm^2$. Briefly, the nozzle used for dispensing the dispensed product of FIG. 13B is pictorially represented in FIG. 5B where the first portion dispensing cross sectional area (i.e., first outlet orifice) is 3 $mm^2$ and the second portion dispensing cross sectional area (i.e., second outlet orifice) is 24 $mm^2$. The nozzle is placed 2 mm away from the Leneta Card, wherein a central axis of the nozzle is perpendicular relative to the Leneta Card. The speed and amount of the first and second compositions dispensed is controlled by an electronic syringe pump (Fusion 200 Syringe Pump from Chemyx Inc. or equivalent) and syringes (First Portion Syringe: Terumo 5 ml with Diameter of 13 mm; and Second Portion Syringe: Terumo 30 ml with Diameter of 23.1 mm). The syringe pump is adjusted to dispense a total of 0.3 ml of discrete dispensed product (combined volume of first and second portion) at a standard dispensing speed of 15 ml/min for the second portion syringe Terumo 30 ml. Syringes of varying sizes can be appropriately used to get the desired volume and ratio of the discrete dispensed product. The discrete dispensed product is then imaged.

The imaging system includes a light booth with black opaque background on all surrounding four sides. The light booth is illuminated with two LED spotlights (e.g., Solax-iO LED artificial solar light source having a diameter of 8 cm, model LE-9ND65 with Polarizer film 100 mm SQ TS #86187 from Edmund Optics). The spotlights are on opposing sides of the dispensed product at 45 degrees. The distance of the spotlight to the discrete dispensed product is 18 cm. A digital color camera (Camera info: Canon EOS 600D, lens: Canon lens EF 35 mm 1:2 IS USM with Vitacon professional PL 67 mm polarized light filter) is overhead, wherein the camera lens is positioned centered and overhead of the discrete dispensed product. The minimum area of the discrete dispensed product in the captured image is 4000 pixels. Polarizers on both camera lens and spotlights are adjusted to reduce specular reflections. A 24 standard color checker chart for color calibration is used (e.g.,"Color Checker Passport" chart from X-rite Corporation Inc, Grand Rapids, MI, USA, or equivalent). The Leneta Card and color checker chart are arranged so as to be in the same field of view. The camera exposure is set such that a histogram of the digital image shows the image intensities to be within the upper half of the dynamic range of the digital image without reaching the upper limit. This ensures that there is no saturation (i.e., clipping) and the image is well exposed (but not overexposed). The discrete dispensed product is dispensed onto the Leneta Card at the predetermined location. The image is taken within 3 seconds after dispensing. A schematic, top view, representation of images of discrete dispensed products are provided in FIGS. 13A and 13B. The second portion is transparent while the first portion is with a color. Further, as the first discrete dispensed product (Formulation Example V) includes an orange dye, which can be clearly seen through the transparent second portion, the dispensed product appears as an orange color core (the first portion) enveloped in a transparent shell (the second portion) to a naked eye which gives an image of a beautiful and premium looking discrete dispensed product. The resulting image is subject to image analysis to ultimately determine the percentage by which the second portion surrounds a maximum perimeter of the first portion.

Firstly, a background is captured. A photo is taken of a white sheet of paper that fills the field of view. For purposes of clarification, this does not include the Leneta card or the Color Checker Chart. Noise from the image is removed and the resulting image is converted to a "percentage image" wherein each pixel represents the percentage of maximum intensity in the image. An image, with dispensed product on Leneta card and color checker chart next to it, is aquired. A "flat field" background corrected image is created by taking the image of the dispensed product with color checker chart next to it and dividing this image by the "percentage image."

Secondly, the background corrected image is convered to a calibrated CIELAB color space image. The RGB values of each chip are measured in the Color Checker Chart. A transform is developed that converts camera RGB values into calibrated tristimulus XYZ values. The transform is then applied to every pixel in the background corrected image to produce a calibrated XYZ image. In turn, the XYZ image is converted into a calibrated CIELAB color space image by using analytical CIE formulas, for the D65 illuminate, 10 degree observer per ASTM Standard E308-01. "LAB" and "XYZ" refers to the commonly recognized color space specified by the International Commission on Illumination ("CIE").

Thirdly, the Delta E image is computed. The color of the white Leneta Card is defined as the reference color. The color difference is calculated, compared to the reference color, using CIE Delta E 2000 formula (ASTM Standard No. D2244-16) for each pixel, to convert the calibrated CIELAB color space image into a color difference image. In some preferred examples of the present invention: the second portion is at least partially transparent or transparent; and the first portion non-transparent, preferably opaque, more preferably opaque and with a color. In such examples, the second portion is slightly darker than the white Leneta card and thus may have some amount of color. To this end, the second portion may have a Delta E in the 5-20 range (as compared to the reference color). The first portion, in these preferred examples, typically has a much different color than the white Leneta card and the second portion. That is to say, the Delta E of the first portion is usually designed to be higher than the Delta E of the second portion, e.g., more than 10.

Fourthly, the portion of the image corresponding to the entire discrete dispensed product is isolated from the remainder of the calibrated Delta E image (corresponding, for example, to the white Leneta card substrate background and color checker) such that the only image content remaining corresponds to the dispensed product, i.e., a "dispensed product mask" image. If the analysis is performed using a digital image analysis software package, this may be performed, for example, through the use of an appropriate threshold to define a dispensed product mask or by manually constructing a dispensed product mask, that once applied, only the area of the corresponding to the dispensed product remains and all other pixels have no value.

In some cases for example, when the second portion is transparent, there can be an optical effect where a "halo effect" is created around the dispensed product. This halo effect is an optical effect where light reflecting/refracting from the first portion interacts inside of the second portion before escaping to produce the optical effect next to the perimeter of the dispensed product. In such circumstances, uniformly reduce (such as through pixelwise image "erosion") the outer dispensed product mask just enough to remove any halo effect artifacts in the image, but such erosion should not diminish the dispensed product area by more than 8%, perferrably no more than 5% of the dispensed product area.

Fifthly, a first portion mask image is generated. The Delta E value of each pixel in the dispensed product mask is extracted (as in step 3 above). Using the Otsu thresholding method, the delta E threshold is used to define the first portion mask. If halo effect is observed and dispensed product mask is eroded, this eroded dispensed product mask is used for first portion mask generation.

Sixthly, perimeter masks of the respective inner first portion mask and the dispensed product mask are created. These masks are only of the outer perimeter, preferably only a single pixel wide.

Seventhly, the lengths of the: perimeter of the dispensed product; perimeter of the first portion; and the overlapping perimeter (if any), are computed from the perimeter masks. The length of the first portion perimeter is measured from the first portion perimeter mask. The length of the dispensed product perimeter is measured from the dispensed product perimeter mask. That portion, if any, of first portion surrounded by second portion is identified and measured to provide an "overlapping perimeter length" (L)—schematically represented in FIG. 11 and referenced as 168. The terms "overlapping perimeter length" and "maximum perimeter of the first portion" are used interchangeably.

Lastly, the percentage by which the second portion surrounds a maximum perimeter of the first portion is determined. The overlapping perimeter length (L) is divided by the first portion perimeter length (P) and multiplied by 100% and is reported to the nearest integer percent. FIG. 14 pictorially represents a top view of a discrete dispensed product (91) in which a first portion (95) is partially surrounded by a second portion (93). A first portion perimeter (97) is the length of the entire perimeter of the first portion (95), which is referred to as P for computing Percentage Surrounding. A discrete dispensed product perimeter (92) is the length of the entire perimeter of the dispensed product (91). The overlapping perimeter length (98) is that length of the first portion perimeter (97) that is surrounded by the second portion (93), which is referred to as L for computing Percentage Surrounding.

In those circumstances where the first portion and second portion have a "Delta E test method" ("PDETM") value of less than or equal to 70, the Otsu thresholding in the fifth step above utilizes a chroma thresholding to determine the first portion mask image. In this case, a chroma image is needed. Chroma image is computed from "CIELAB color space image" using A and B values from the CIELAB color space by converting each pixel into a chroma value. The formula this conversion is chroma=sqrt(A^2+B^2).

Turning back to FIGS. 13A and 13B, the first portion perimeter as well as the overlapping perimeter length of the respective dispensed product are identified by the above method. The electronic syringe pump as described above was used to dispense the discrete dispensed product pictorally represented in FIGS. 13A and 13B. The first portion perimeter of the discrete dispensed product of FIG. 13A is 1.94 cm and the overlapping perimeter length is also 1.94 cm. As the overlapping perimeter length and the first portion perimeter are same thus the second portion completely (i.e., 100%) surrounds the first portion in the discrete dispensed product represented in FIG. 13A. And for the discrete dispensed product of FIG. 13B, after accounting for 7.8% area erosion (to counter halo effect), the first portion perimeter is 1.99 cm and overlapping perimeter length is 1.17 cm. As for FIG. 13B, the second portion surrounds 59% of the maximum perimeter of the first portion [(1.17÷1.99)*100].

E image is calculated. Then the Dispensed product mask image (generated in step four with erosion to counter for halo effects) and the first portion mask image (generated in the fifth step) are used in the sixth step to create dispensed product perimeter mask and first portion perimeter mask respectively. Finally, in the seventh step the perimeter masks created in the sixth step are used to identify the length of discrete dispensed product perimeter (which is 5.72 cm), length of the first portion perimeter (which is 1.94 cm) and the overlapping perimeter length (which is computed to be 1.94 cm). From the above data, divide the overlapping perimeter length (L) with the first portion perimeter (P) and multiply by 100 [(1.94÷1.94)*100] to get the percentage by which the second portion surrounds the maximum perimeter of the first portion.

Similarly, this method can be applied to the discrete dispensed product (166) of FIG. 11 which is analogous to the comparative Example B on consumer study represented by the discrete dispensed product 66 in FIG. 10B. Herein, the length of abutment (168) is the overlapping perimeter length (L) or the maximum perimeter of the first portion. This length of abutment, which is used computing the percentage by which the second portion (167), surrounds the maximum perimeter of the first portion (169) that is determined to be 25.6% (also indicated in data section of Comparative Example I in Table 1, FIG. 7E).

Length: Height Ratio

The length and height of a discrete dispensed product is measured and ratios thereof described. The dispensed product is dispensed, wherein the nozzle of the dispenser is directed perpendicularly and remains stationary during dispensing, on a flat and horizontal Leneta Card and, within 3 seconds, is imaged from the side from which dimensions are obtained. The dispensing nozzle is placed 2 mm away from the Leneta Card during dispensing. The camera is positioned such that the projection distance of the dispensed product away from the Leneta Card surface is maximized. The card is rotated such that the projection length of the planar contact surface of the dispensed product is maximized. The camera and camera lens (Camera info: Canon EOS 600D, lens: Canon lens EF 35 mm 1:2 IS USM) are positioned so that it is perpendicular to the length and in the same planar contact surface of the dispensed product. A lighting source located above the dispensed product illuminates the dis-

TABLE 5

Percentage of Second Portion Surrounding Maximum Perimeter of First Portion

| Formulation Ex. | FIG. of Product (FIG. of Nozzle) | Perimeter Length (cm) | | | % Second Portion surrounding Max Perimeter of First Portion |
|---|---|---|---|---|---|
| | | Discrete Dispensed Product | First Portion Maximum Perimeter | Overlapping Perimeter Length (L) | |
| V | FIG. 13A (FIG. 5A) | 5.72 | 1.94 | 1.94 | 100% |
| V | FIG. 13B (FIG. 5B) | Before Erosion 4.03 After 7.8% area erosion (to account for halo effect) 3.52 | Not applicable 1.99 (after erosion) | Not applicable 1.17 (after erosion) | Not applicable 59% |

To summarize, the discrete dispensed product of FIG. 13A is used in the above method. In the first step background corrected image is obtained, which is calibrated to CIELAB color space image in the second step. In the third step, delta pensed product to provide sufficient contrast between the dispensed product and the background. The captured image should have a spatial resolution of no fewer than 350 pixels/cm. The image is preferably captured along with a ruler or spatial calibration target located at the same focal distance as the dispensed product.

An image of the dispensed product is captured using the imaging setup described. The maximum length of the dispensed product is assessed at its planar contact surface, i.e., where the dispensed product meets the Leneta card, is measured as the length (L), and is recorded in cm and reported to the nearest hundredth. The maximum projection distance of the dispensed product orthogonally away from the plane of the Leneta card is measured as the height (H) of the dispensed product, and is recorded in cm and reported to the nearest hundredth. The dimensionless quotient L/H is calculated and reported to the nearest hundredth.

Flowability

The Discrete Dispensed Product Flowability Test Method ("DDPFTM") is herein described to determine the speed of movement of a first portion or second portion (herein after referred to collectively as a "portion") at the angle of 45 degrees on a flat surface at 25° C. (reported as cm/min). A syringe (Terumo 1 cc syringe or equivalent), is filled with 0.3 ml of a composition corresponding to the subject portion, and the 0.3 ml filled composition is dispensed out within 2 seconds on a horizontally placed Leneta Card (Opacity Card Form 2A, Leneta Company, Inc, Mahwah, NJ, USA, or equivalent) forming a droplet of the portion on the Leneta Card. The dispensing syringe is placed 2 mm away from the Leneta Card during dispensing and remains stationary during dispensing Immediately thereafter (within 3 seconds), the Leneta Card is tilted (within 0.5 seconds) at 45 degrees on a tilt table. The distance traversed by the leading edge of the droplet during 1 minute is measured to the nearest 0.5 mm. The flowability is defined as the speed with units cm/minute and is reported to the nearest hundredth. If the droplet reaches the edge of the Leneta card in less than 1 min, then record the time that the leading edge of the droplet takes to move 10 cm on the Leneta Card to calculate the speed.

Oscillatory Rheometry

The Portion Oscillatory Rheometry Test Method ("PORTM") is used to determine "Crossover Stress," reported in units of Pa, of a portion (e.g., the first or second portion of a discrete dispensed product) as described herein. A controlled-strain rotational rheometer (such as Discovery HR-2, TA Instruments, New Castle, DE, USA, or equivalent) capable of portion sample temperature control (using a Peltier cooler and resistance heater combination) is used for this test. Before the test, each portion sample is stored in a separated container and placed in a temperature controlled lab (23±2° C.) overnight. During the test, the lab temperature is controlled at 23±2° C. The rheometer is operated in a parallel plate configuration with 40-mm crosshatch stainless steel parallel-plate tooling. The rheometer is set at 25° C. Approximately 2 ml of the portion sample is gently loaded onto peltier plate using a spatula from the sample container to prevent a change in the portion sample structure, and any excess protruding sample is trimmed once the gap reaches 1000 µm after sample loading. The portion sample is then equilibrated at 25° C. for at least 120 seconds before measurement starts. In case a different rheometer is used, extend the equilibrium time appropriately to ensure the portion sample temperature achieves 25° C. before the test. The test commences with rheometer increased from strain amplitude 0.1% to 1000% in logarithmic mode with oscillation frequency fixed at 1 Hz (that is, one cycle per second) at 25° C. For each strain amplitude sampled, the resulting time-dependent stress is analyzed according to the customary logarithmic oscillatory strain formalism, known to those of skill in the art, to obtain the storage modulus (G') and loss modulus (G") at each step. A plot is made in which G' and G" (both expressed in units of Pascals, vertical axis) are plotted versus the strain amplitude (percent strain, horizontal axis). The lowest strain amplitude at which the traces for G' and G" cross (that is, when $\tan(\delta)=G"/G'=1$) is recorded. This point is defined as crossover point and the oscillation stress at this point is defined as the "Crossover Stress" and is reported to nearest whole number in units of Pa. Rheological properties measured by the rheometer provided by the present disclosure include, but are not limited to, storage modulus G', a loss modulus G", loss factor $\tan(\delta)$. Crossover point, is extracted using TRIOS software (provided by TA instrument) and is applicable for other equivalent rheology software.

Opacity Measure

The Portion Opacity Test Method ("POTM") is used to determine the opacity of a first portion or second portion (of the discrete dispensed product). Results are reported as a percentage, wherein higher the percentage the greater is the opacity of the sample. Generally, the opacity is the quality of a material that does not allow light to pass through. Higher percentage values mean greater hiding power and thus less transparency. A spectrophotometer that can deliver tristimulus values CIE XYZ under CIE D65 lighting conditions across the visible spectrum (such as Spectrophotometer CM-3600A, Konica Minolta, Japan, or equivalent) is used for this method. The spectrophotometer is operated under conditions to deliver 1931 CIE defined tristimulus XYZ values with 2° observer and D65 illuminant Portion samples are evaluated using a 10 mm path length in a plastic cell (such as CM-A131, Konica Minolta, Japan or equivalent), reflectance measurement, a 25.4 mm aperture opening at the specimen surface, specular component excluded. Two sets of tristimulus values are necessary to calculate opacity—one with the product's 10 mm sample cell in front of a white background and the other in front of a black background. Acceptable white backgrounds include the white portion of an opacity card (such as Opacity Card Form 2A, Leneta Company, Inc, Mahwah, NJ, USA, or equivalent) and acceptable black backgrounds are the black portion of an opacity card (such as Opacity Card Form 2A, Leneta Company, Inc, Mahwah, NJ, USA, or equivalent). Opacity is determined by calculating the quotient of the Y tristimulus value using the black background divided by the Y tristimulus value using the white background and multiplying by 100%. Opacity is reported to the nearest integer percentage.

Delta E*

The Portion Delta E* Test Method ("PDETM") is used to determine the color difference between the first portion and the second portion and yield a Delta E* value. Delta E* is the calculated Euclidean distance between two color stimuli in the CIELAB color space. For a sample product, CIELAB values of $L^*_2$, $a^*_2$, $b^*_2$, the color difference or delta E* ($\Delta E^*$) between a second product with CIELAB values $L^*_1$, $a^*_1$, $b^*_1$ is given by:

$$\Delta E^* = \sqrt{(L^*_2 - L^*_1)^2 + (a^*_2 - a^*_1)^2 + (b^*_2 - b^*_1)^2}$$

A spectrophotometer that can deliver CIELAB under CIE D65 illuminant conditions across the visible spectrum (such as Spectrophotometer CM-3600A, Konica Minolta, Japan, or equivalent) is used for this method. The spectrophotometer is operated under conditions to deliver CIELAB values with 2° observer and D65 illuminant Portion samples are evaluated using a 10 mm path length in a plastic cell (such as CM-A131, Konica Minolta, Japan or equivalent), reflectance measurement, a 25.4 mm aperture opening at the specimen surface, and specular component excluded. A white background (such as the white portion of Opacity Card Form 2A, Leneta Company, Inc, Mahwah, NJ, USA, or equivalent) is used behind the 10 mm product sample. L*, a*, and b* values are determined sequentially for both the first portion and the second portion and are recorded to the nearest hundredth. The above formula is used to calculate Delta E*, which is reported to the nearest integer.

Results are reported in Tables 1, 2, and 3 of FIGS. 7A-7E; FIGS. 8A-8E; FIGS. 9A-9E, respectively.

It will be understood that reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm". All numeric ranges described herein are inclusive of narrower ranges; delineated upper and lower range limits are interchangeable to create further ranges not explicitly delineated. Embodiments described herein can comprise, consist essentially of, or consist of, the essential components as well as optional pieces described herein. As used in the description and the appended claims, the singular forms "a," "an," and "the" are intended to include the plural forms as well, unless the context clearly indicates otherwise.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A discrete dispensed personal care product comprising: a first portion; and a second portion completely surrounding the first portion, wherein the second portion comprises a Crossover Stress assessed by a Portion Oscillatory Rheometry Test Method ("PORTM"), wherein the Crossover Stress of the second portion is equal to or greater than 10 Pascals (Pa); wherein the first portion remains visually distinct from the second portion within the dispensed product; wherein the first portion is fully suspended in the second portion; wherein the discrete dispensed product substantially retains its dispensed shape after being dispensed; and wherein the first and second portions each comprise a structuring agent chosen from an alkyl hydroxyalkyl cellulose ether, cross linked polyacrylate, a cross linked polymer comprising an acryloyldimethyltaurate as a monomer, or mixtures thereof.

2. The discrete dispensed personal care product according to claim 1, wherein the Crossover Stress of the second portion is from about 10 Pa to about 50 Pa.

3. The discrete dispensed personal care product according to claim 1, wherein either:
   (i) the first portion comprises a skin care active, and the second portion comprises a pH lower than the first portion; or
   (ii) the second portion comprises a skin care active, and the first portion comprises a pH lower than the second portion;
   wherein the second or first portion comprising a pH lower than the first or second portion respectively, comprises a pH from about 2.5 to about 5.

4. The discrete dispensed personal care product according to claim 1, wherein the second portion comprises a speed assessed by a Discrete Dispensed Product Flowability Test Method ("DDPFTM"), wherein the speed of the second portion is from 0 to about 3 cm/minute.

5. The discrete dispensed personal care product according to claim 1, wherein the first portion comprises a speed assessed by a Discrete Dispensed Product Flowability Test Method ("DDPFTM"), wherein the speed of the first portion is from 0 to about 3 cm/minute.

6. The discrete dispensed personal care product according to claim 1, wherein the Crossover Stress of the second portion is from about 10 Pa to about 120 Pa.

7. The discrete dispensed personal care product according to claim 1, wherein the first portion comprises a Crossover Stress assessed by PORTM, wherein the Crossover Stress of the first portion is from about 5 to about 120 Pa.

8. The discrete dispensed personal care product according to claim 1, wherein a length of the discrete dispensed product is from about 0.5 cm to about 2.5 cm, wherein the length is the longest dimension measured along a planar contact surface of the discrete dispensed product.

9. The discrete dispensed personal care product according to claim 1, wherein the discrete dispensed product comprises a height from about 0.2 cm to about 2 cm, wherein the height is measured in a plane orthogonal to the planar contact surface of the discrete dispensed product.

10. The discrete dispensed personal care product according to claim 1, wherein the ratio of length to height of the discrete dispensed product, is from about 5:1 to about 1:2.

11. The discrete dispensed personal care product according to claim 1, wherein the first portion has an Opacity Percentage assessed by a Portion Opacity Test Method ("POTM"), wherein the Opacity Percentage of the first portion is from 0% to about 60%.

12. The discrete dispensed personal care product according to claim 1, wherein the second portion has an Opacity Percentage assessed by a Portion Opacity Test Method ("POTM"), wherein the Opacity Percentage of the second portion is from 0% to about 60%.

13. The discrete dispensed personal care product according to claim 1, wherein the first portion and the second portion each has an Opacity Percentage assessed by a Portion Opacity Test Method ("POTM") wherein the difference in the Opacity Percentage between the first portion and the second portion is from about 50% to 100%.

14. The discrete dispensed personal care product according to claim 1, further has a Delta E* value between the first portion and the second portion, assessed by a Portion Delta E* Test Method ("PDETM"), wherein the Delta E* value is from about 35 to about 200.

15. The discrete dispensed personal care product according to claim 1, wherein the second portion is at least partially transparent, and the product is a skin care product.

16. The discrete dispensed personal care product according to claim 1, wherein the discrete dispensed product comprises a substantially hemispherical shape.

\* \* \* \* \*